US012447167B2

(12) United States Patent
Yamamura et al.

(10) Patent No.: US 12,447,167 B2
(45) Date of Patent: Oct. 21, 2025

(54) GM-CSF-PRODUCING T-CELL CONTROL AGENT AND Th1/Th2 IMMUNE BALANCE REGULATOR

(71) Applicant: National Center of Neurology and Psychiatry, Kodaira (JP)

(72) Inventors: Takashi Yamamura, Kodaira (JP); Daisuke Noto, Kodaira (JP); Sachiko Miyake, Kodaira (JP)

(73) Assignee: NATIONAL CENTER OF NEUROLOGY AND PSYCHIATRY, Kodaira (JP)

( * ) Notice: Subject to any disclaimer, the term of this patent is extended or adjusted under 35 U.S.C. 154(b) by 0 days.

(21) Appl. No.: 15/310,056

(22) PCT Filed: Apr. 28, 2015

(86) PCT No.: PCT/JP2015/062854
§ 371 (c)(1),
(2) Date: Nov. 9, 2016

(87) PCT Pub. No.: WO2015/174278
PCT Pub. Date: Nov. 19, 2015

(65) Prior Publication Data

US 2017/0151270 A1 Jun. 1, 2017

(30) Foreign Application Priority Data

May 13, 2014 (JP) ................................ 2014-099587

(51) Int. Cl.
*A61K 31/7032* (2006.01)
*A61K 31/715* (2006.01)

(52) U.S. Cl.
CPC ........ *A61K 31/7032* (2013.01); *A61K 31/715* (2013.01)

(58) Field of Classification Search
CPC .............. A61K 1/7032; A61K 31/7032; A61K 31/7028
(Continued)

(56) References Cited

U.S. PATENT DOCUMENTS

| | | | |
|---|---|---|---|
| 6,531,453 | B1 | 3/2003 | Taniguchi et al. |
| 2008/0260774 | A1 | 10/2008 | Wong et al. |

(Continued)

FOREIGN PATENT DOCUMENTS

| | | | |
|---|---|---|---|
| EP | 1437358 A1 | 7/2004 | |
| JP | 2004131481 A | 4/2004 | |

(Continued)

OTHER PUBLICATIONS

Ponomarev et al. (The Journal of Immunology, 2007, 178: 39-48).*
(Continued)

*Primary Examiner* — Eric Olson
(74) *Attorney, Agent, or Firm* — SQUIRE PATTON BOGGS (US) LLP

(57) ABSTRACT

The present invention provides a GM-CSF-producing T-cell control agent comprising a glycolipid compound represented by the following formula (I) or a salt thereof as an active ingredient:

[Chemical Formula 1]

(I)

(Continued)

wherein $R^1$ represents an aldopyranose residue, $R^2$ represents a hydrogen atom or a hydroxy group, $R^3$ represents $-CH_2-$, $-CH(OH)-CH_2-$, or $-CH{=}CH-$, $R^4$ represents a hydrogen atom or $CH_3$, x is 0 to 35, and y and z each represent an integer that satisfies y+z=0 to 3.

7 Claims, 9 Drawing Sheets

(58) Field of Classification Search
USPC ........................................................... 514/25
See application file for complete search history.

(56) References Cited

U.S. PATENT DOCUMENTS

| | | | | |
|---|---|---|---|---|
| 2012/0100139 | A1 | 4/2012 | Thompson et al. | |
| 2017/0151270 | A1* | 6/2017 | Yamamura | A61P 37/02 |
| 2023/0405033 | A1* | 12/2023 | Yamaura | A61P 43/00 |

FOREIGN PATENT DOCUMENTS

| | | | | |
|---|---|---|---|---|
| JP | 2007230976 | A | 9/2007 | |
| JP | 2007230977 | A | 9/2007 | |
| JP | 4064346 | B2 | 3/2008 | |
| JP | 2010523724 | A | 7/2010 | |
| JP | 2012504425 | A | 2/2012 | |
| JP | 2013116912 | A | 6/2013 | |
| WO | WO 03/016326 | A1 | 2/2003 | |
| WO | WO 2006/065613 | A2 | 6/2006 | |
| WO | WO 2012/151279 | A2 | 11/2012 | |
| WO | WO 2013/033283 | A1 | 3/2013 | |
| WO | WO 2014/042226 | A1 | 3/2014 | |
| WO | WO-2015154195 | A1 * | 10/2015 | A61K 31/17 |

OTHER PUBLICATIONS

Reagan-Shaw et al. (FASEB J. 22, 659-661 (2007)).*
Ansel et al. (Pharmaceutical dosage forms and drug delivery systems; Book/Illustrated—7th ed., 1999).*
Notification of Transmittal of Translation of the International Preliminary Report on Patentability mailed Nov. 24, 2016 for PCT/JP2015/062854, 6 pages.
Extended European Search Report dated Jan. 8, 2018 for EP15792520.7, 12 pages.
Li, Qian, et al: "Rapid identification of immunostimulatory a-Galactosylceramides using synthetic combinatorial libraries", Journal of Combinatorial Chemistry, Nov. 1, 2007, vol. 9, No. 6, pp. 1084-1093, XP055304906.
Ndonye, Rachel M., et al: "Synthesis and evaluation of sphinganine analogues of KRN7000 and OCH", The Journal of Organic Chemistry, Dec. 1, 2005, vol. 70, No. 25, pp. 10260-10270, XP055242046.
Walker, Kyle M., et al: "Preventing and curing citrulline-induced autoimmune arthritis in a humanized mouse model usibng a Th2-polarizing Inkt CELL agonist", Immunology and Cell Bio, Jul. 1, 2012, vol. 90, No. 6, pp. 630-639, XP009174076.
Alvaro-Garcia, Jose M., et al; "Cytokines in chronic inflammatory arthritis. VI. Analysis of the synovial cells involved in granulocyte-macrophage colony-stimulating factor production and gene expression in rheumatoid arthritis and its regulation by IL-1 and tumor necrosis factor-a1", Journal of Immunology, vol. 146, pp. 3365-3371, May 15, 1991, 7 pages.
Araki, Manabu, et al; "Synthetic glycolipid ligands for human iNKT cells as potential therapeutic agents for immunotherapy", Current Medicinal Chemistry, vol. 15, pp. 2337-2345 (Oct. 2008), 10 pages.
Campbell, Ian K., et al; "Granulocyte-macrophage colony stimulating factor exacerbates collagen induced arthritis in mice", Annals of the Rheumatic Diseases, vol. 56, pp. 364-368 (1997), 6 pages.
Campbell, Ian K., et al; "Protection from collagen-induced arthritis in granulocyte-macrophage colony-stimulating factor-deficient mice", Journal of Immunology, vol. 161, pp. 3639-3644 (1998), 7 pages.
Hamilton, John A., "Colony-stimulating factors in inflammation and autoimmunity", Nature Reviews | Immunology, vol. 8, pp. 533-544 Jul. 2008, 12 pages.
Miyamoto, Katsuichi, et al; "A synthetic glycolipid prevents autoimmune encephalomyelitis by inducing TH2 bias of natual killer T cells", Letters to Nature, vol. 413, pp. 531-534 (Oct. 2001), 4 pages.
Wan, Chi-Keung, et al; "The cytokines IL-21 and GM-CSF have opposing regulatory roles in the apoptosis of conventional dendritic cells", Immunity, vol. 38, pp. 514-527, Mar. 21, 2013, 14 pages.
Xu, Wei dong, et al.; "Cytokines in chronic inflammatory arthritis. II. Granulocyte-macrophage colony-stimulating factor I rheumatoid synovial effusions", The American Society for Clinical Investigation, Inc., vol. 83, pp. 876-882 (Mar. 1989), 8 pages.
International Search Report mailed Aug. 11, 2015 for PCT/JP2015/062854, 2 pages.
Neimeyer, et al., "Natural killer T-cell characterization through gene expression profiling: an account of versatility bridging T helper type 1 (TH1), Th2 and Th17 immune responses", Immunology 2007, vol. 23, Issue 1, pp. 45-56.
Okita, et al: "A set of genes associated with the interferon-y response of lung cancer patients undergoing x-galactosylceramide-pulsed dendritic cell therapy", Cancer Science Aug. 31, 2010, vol. 101, No. 11, pp. 2333-2340.
Toba, et al: "Synthesis and biological evaluation of truncated x-galactosylceramide derivatives focusing on cytokine induction profile", Bioorganic & Medicinal Chemistry Mar. 20, 2012, vol. 270, No. 9, pp. 2850-2859.

* cited by examiner

GM-CSF-PRODUCING T-CELL CONTROL AGENT AND Th1/Th2 IMMUNE BALANCE REGULATOR

TECHNICAL FIELD

The present invention relates to a GM-CSF-producing T-cell control agent comprising a α-galactosylceramide derivative as an active ingredient. The present invention also relates to a Th1/Th2 immune balance regulator. The present invention further relates to an agent for use in the treatment of diseases caused by increase in GM-CSF concentration and an agent for use in the regulation of Th1/Th2 immune balance.

BACKGROUND ART

GM-CSF (granulocyte•macrophage colony-stimulating factor) is a glycoprotein that is known to also participate in a hematopoietic mechanism, for example, by acting on pluripotent hematopoietic stem cells as a hematopoietic growth factor, in addition to acting on myeloid progenitor cells of granulocytes and macrophages and promoting their differentiation or maturation (Non Patent Literature 1). It is known that GM-CSF is mainly produced from activated T-cells, but is also produced from various cells such as macrophages, fibroblasts, and endothelial cells and also functions as an inflammatory cytokine promoting the growth or activity of neutrophils or eosinophils, when inflammation has occurred due to bacterial infection, trauma, autoimmune diseases, or the like (Non Patent Literature 1). The elevation of expression of GM-CSF is found in various inflammatory sites such as arthritis, psoriasis, and lung diseases, suggesting involvement in the induction of inflammation.

Although the inflammation-inducing effect of GM-CSF is originally a body defense response, an excessive response may also become a new-onset process of pathogenesis. For example, it has been revealed that at a local arthritis lesion of RA (chronic rheumatoid arthritis), GM-CSF is present in synovial joints, suggesting the association of the onset of RA with an excessive amount of GM-CSF (Non Patent Literatures 2 and 3). Also, while SIRS (systemic inflammatory response syndrome) is fatal organ dysfunction that is induced by bacterial infection, trauma, or burning, it has been revealed that its cause is an acute inflammatory response caused by large amounts of inflammatory cytokines, including GM-CSF, released into blood due to the bacterial infection or the like.

Thus, if GM-CSF is used as a target of anti-inflammatory therapy and its in vivo abundance is reduced or its functions are inhibited, it can be expected that inflammatory diseases can be mitigated or cured. In actuality, it has been shown that inflammatory diseases of various inflammation models including arthritis were able to be prevented or cured in the functional inhibition experiments of GM-CSF with neutralizing antibodies by in vivo experiments of mice (Non Patent Literatures 4 and 5).

Also, in Patent Literature 1, an antibody specific for GM-CSF and a functional fragment thereof are disclosed as antibody drugs for the treatment of inflammatory diseases such as rheumatoid arthritis.

In Patent Literature 2, a therapeutic agent for atopic dermatitis, a cosmetic, a food product, and a skin preparation for external use supplemented with a GM-CSF production inhibitor comprising an extract of a leaf or/and a voluble stem of a plant of the genus *Wisteria*, an extract of *Alchornea castaneifolia*, an extract of *Sesamum indicum*, an extract of

*Undaria pinnatifida*, or a tripeptide which is lysine-valine-lysine or/and a derivative thereof as an active ingredient are disclosed. Also, in Patent Literature 3, a therapeutic agent for atopic dermatitis and a food product comprising at least one or more selected from an extract of *Rubiaceae uncaria*, an extract of *Aquifoliaceae ilex*, an extract of *Perilla frutescens*, an extract of *Cnidium officinale*, an extract of *Opuntia streptacantha*, an extract of *Justicia gendarussa*, an extract of *Sparassis crispa*, and L-ergothioneine as an active ingredient are disclosed.

CITATION LIST

Patent Literature

Patent Literature 1: JP 2013-116912 A

Patent Literature 2: JP 2007-230976 A

Patent Literature 3: JP 2007-230977 A

Non Patent Literature

Non Patent Literature 1: Hamilton J A, 2008, Nature Reviews Immunology, 8: 533-544

Non Patent Literature 2: Alvaro-Gracia J M, et al., 1991, J Immunol., 146: 3365-3371

Non Patent Literature 3: Xu W D, et al., 1989, J Clin Invest, 83: 876-882

Non Patent Literature 4: Campbell I K, et al., 1997, Ann. Rheum. Dis., 56: 364-368

Non Patent Literature 5: Campbell I K, et al., 1998, J. Immunol., 161: 3639-3644

SUMMARY OF INVENTION

Technical Problem

However, antibody drugs comprise a protein as an active ingredient and therefore, are difficult to orally administer and are usually administered by injection. Thus, invasiveness is high as compared with oral administration, and it cannot be said that administration is easy. Furthermore, the antibody drugs present the problem that production cost is high as compared with conventional low-molecular drugs. Particularly, because the antibody drugs require administration in a large amount as compared with other protein drugs, for producing adequate effects, treatment cost is further increased.

However, the inventions described in Patent Literatures 2 and 3 leave a problem in the stability of effects, because the active ingredients are mainly extracts of plants and are in a crude state. Furthermore, disclosed therein are percutaneous agents for relatively mild dermal inflammatory responses such as atopic dermatitis, and effects on serious inflammatory diseases such as RA or SIRS cannot be expected.

Meanwhile, as mentioned above, cells mainly producing GM-CSF are activated T-cells, and if the in vivo growth of GM-CSF-producing T-cells is suppressed or the ability of the T-cells to produce GM-CSF can be suppressed by orally administrable low-molecular drugs, the in vivo amount of GM-CSF can be efficiently reduced, probably leading to effective therapeutic drugs for various inflammatory diseases. However, reports on agents capable of using T-cells producing GM-CSF as a target and suppressing their growth or suppressing their ability to produce GM-CSF have not yet been known.

An object of the present invention is to develop an agent comprising, as an active ingredient, a low-molecular compound that can reduce the amount of GM-CSF in vivo by suppressing the growth of the target T-cells producing GM-CSF or the ability to produce GM-CSF.

Solution to Problem

The present inventors have previously identified a derivative of α-galactosylceramide, which is a synthetic glycolipid ligand inducing the selective production of IL-4 production by stimulating NKT-cells (Japanese Patent No. 4064346). This derivative has the activity of controlling the suppression of Th1 cellular immune responses via IL-4 production and has the effect of preventing or treating EAE (experimental autoimmune encephalomyelitis) consisting essentially of autoimmune inflammation in the central nervous system by oral or intraperitoneal administration (Miyamoto K et al., 2001, Nature, 413: 531-534). When the derivative is orally administered to mice, the suppression of Th1 cellular immune responses via selective IL-4 production by NKT-cells activated by this derivative takes place so that EAE is inhibited. Also, the derivative induces the dominant production of Th2 cytokines for human NKT-cells (Araki M, et al., 2008, Current Medicinal Chemistry, 15: 2337-2345). Hence, it has been suggested that the derivative of α-galactosylceramide becomes a therapeutic drug for human MS (multiple sclerosis).

In order to search for novel drug efficacy of the derivative of α-galactosylceramide (hereinafter, also referred to as the "synthetic glycolipid of the present invention"), as a result of testing T-cell subfractions in peripheral blood in the oral single dose test of the derivative targeting normal subjects, the tendency has been found in which a GM-CSF-producing CD4-positive memory T-cell fraction and a GM-CSF-producing CD8-positive T-cell fraction significantly decrease as compared with pre-administration values. Furthermore, as a result of orally administering the synthetic glycolipid of the present invention to mice, it has been revealed that GM-CSF production from lymph node T-cells is significantly suppressed by low-dose administration. Moreover, it has been revealed that the synthetic glycolipid of the present invention exerts action and effect on humans even at a much smaller dose than a dose predicted from tests results for model animals.

The present invention has been made on the basis of the new findings mentioned above and provides the followings:

(1) A GM-CSF-producing T-cell control agent comprising a glycolipid compound represented by the following formula (I) or a salt thereof as an active ingredient:

[Chemical Formula 1]

(I)

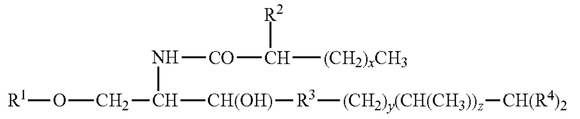

wherein $R^1$ represents an aldopyranose residue, $R^2$ represents a hydrogen atom or a hydroxy group, $R^3$ represents $—CH_2—$, $—CH(OH)—CH_2—$, or $—CH{=}CH—$, $R^4$ represents a hydrogen atom or $CH_3$, x is 0 to 35, and y and z each represent an integer that satisfies y+z=0 to 3.

(2) The GM-CSF-producing T-cell control agent according to (1), wherein $R^1$ is represented by the following formula (II):

[Chemical Formula 2]

(II)

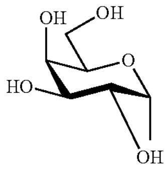

(3) The GM-CSF-producing T-cell control agent according to (2), wherein $R^3$ represents $—CH_2—$ or $—CH(OH)—CH_2—$, and x is 10 to 32.

(4) The GM-CSF-producing T-cell control agent according to (3), wherein $R^3$ represents $—CH(OH)—CH_2—$.

(5) The GM-CSF-producing T-cell control agent according to any of (1) to (4), wherein $R^2$ and $R^4$ each represent a hydrogen atom, x is 11 to 23, and z is 0.

(6) The GM-CSF-producing T-cell control agent according to any of (1) to (5), wherein the GM-CSF-producing T-cell control agent is used such that 0.01 mg or larger and 50 mg or smaller of the glycolipid compound or the salt thereof per dosage is administered to a human.

(7) The GM-CSF-producing T-cell control agent according to (6), wherein the GM-CSF-producing T-cell control agent is used such that 0.01 mg or larger and 50 mg or smaller of the glycolipid compound or the salt thereof per dosage is orally administered to a human.

(8) A GM-CSF lowering agent comprising a glycolipid compound represented by the above formula (I) or a salt thereof as an active ingredient.

The present invention also provides the followings:

(9) A Th1/Th2 immune balance regulator comprising a glycolipid compound represented by the following formula (I) or a salt thereof as an active ingredient, wherein the Th1/Th2 immune balance regulator is used such that 0.01 mg or larger and 50 mg or smaller of the glycolipid compound or the salt thereof per dosage is administered to a human:

[Chemical Formula 3]

(I)

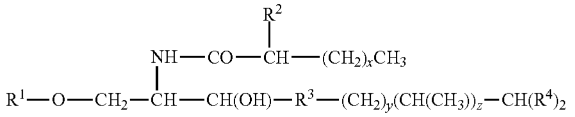

wherein $R^1$ represents an aldopyranose residue, $R^2$ represents a hydrogen atom or a hydroxy group, $R^3$ represents $—CH_2—$, $—CH(OH)—CH_2—$, or $—CH{=}CH—$, $R^4$ represents a hydrogen atom or $CH_3$, x is 0 to 35, and y and z each represent an integer that satisfies y+z=0 to 3.

(10) The Th1/Th2 immune balance regulator according to (9), wherein the Th1/Th2 immune balance regulator is used such that 0.01 mg or larger and 50 mg or smaller of the glycolipid compound or the salt thereof per dosage is orally administered to a human.

(11) The Th1/Th2 immune balance regulator according to (9) or (10), wherein $R^1$ is represented by the following formula (II):

[Chemical Formula 4]

(II)

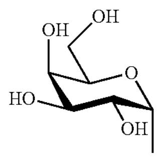

(12) The Th1/Th2 immune balance regulator according to (11), wherein $R^3$ represents —$CH_2$— or —CH(OH)—$CH_2$—, and x is 10 to 32.

(13) The Th1/Th2 immune balance regulator according to (12), wherein $R^3$ represents —CH(OH)—$CH_2$.

(14) The Th1/Th2 immune balance regulator according to any of (9) to (13), wherein $R^2$ and $R^4$ each represent a hydrogen atom, x is 11 to 23, and z is 0.

(15) The Th1/Th2 immune balance regulator according to any of (9) to (14), wherein the Th1/Th2 immune balance regulator is a therapeutic agent or a prophylactic agent for diseases in which Th1/Th2 immune balance is deflected toward Th1 or diseases in which Th1 cells worsen pathological conditions.

(16) The Th1/Th2 immune balance regulator according to any of (9) to (15), wherein the Th1/Th2 immune balance regulator is a therapeutic agent or a prophylactic agent for autoimmune diseases.

The present invention further provides the followings:

(17) An agent for use in the treatment of diseases caused by increase in GM-CSF concentration, the agent comprising a glycolipid compound represented by the following formula (I) or a salt thereof as an active ingredient:

[Chemical Formula 5]

(I)

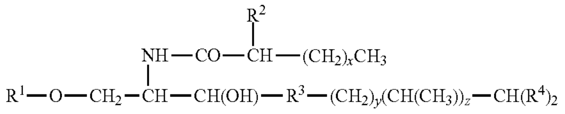

wherein $R^1$ represents an aldopyranose residue, $R^2$ represents a hydrogen atom or a hydroxy group, $R^3$ represents —$CH_2$—, —CH(OH)—$CH_2$—, or —CH═CH—, $R^4$ represents a hydrogen atom or $CH_3$, x is 0 to 35, and y and z each represent an integer that satisfies y+z=0 to 3.

(18) The agent according to (17), wherein $R^1$ is represented by the following formula (II):

[Chemical Formula 6]

(II)

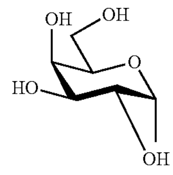

(19) The agent according to (18), wherein $R^3$ represents —$CH_2$— or —CH(OH)—$CH_2$—, and x is 10 to 32.

(20) The agent according to (19), wherein $R^3$ represents —CH(OH)—$CH_2$—.

(21) The agent according to any of (17) to (20), wherein $R^2$ and $R^4$ each represent a hydrogen atom, x is 11 to 23, and z is 0.

(22) The agent according to any of (17) to (21), wherein the agent is used such that 0.01 mg or larger and 50 mg or smaller of the glycolipid compound or the salt thereof per dosage is administered to a human.

(23) The agent according to (22), wherein the agent is used such that 0.01 mg or larger and 50 mg or smaller of the glycolipid compound or the salt thereof per dosage is orally administered to a human.

(24) The agent according to any of (17) to (23), wherein the diseases caused by increase in GM-CSF concentration are chronic inflammatory diseases.

(25) The agent according to any of (17) to (24), wherein the diseases caused by increase in GM-CSF concentration are multiple sclerosis, chronic organ inflammation, or rheumatoid arthritis.

(26) An agent for use in the regulation of Th1/Th2 immune balance, the agent comprising a glycolipid compound represented by the following formula (I) or a salt thereof as an active ingredient, wherein the agent is used such that 0.01 mg or larger and 50 mg or smaller of the glycolipid compound or the salt thereof per dosage is administered to a human:

[Chemical Formula 7]

(I)

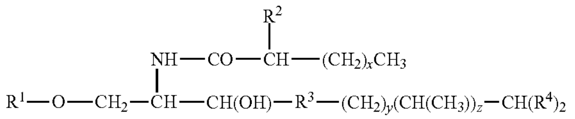

wherein $R^1$ represents an aldopyranose residue, $R^2$ represents a hydrogen atom or a hydroxy group, $R^3$ represents —$CH_2$—, —CH(OH)—$CH_2$—, or —CH═CH—, $R^4$ represents a hydrogen atom or $CH_3$, x is 0 to 35, and y and z each represent an integer that satisfies y+z=0 to 3.

(27) The agent according to (26), wherein the agent is used such that 0.01 mg or larger and 50 mg or smaller of the glycolipid compound or the salt thereof per dosage is orally administered to a human.

(28) The agent according to (26) or (27), wherein $R^1$ is represented by the following formula (II):

[Chemical Formula 8]

(II)

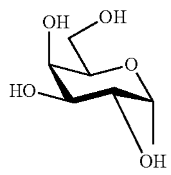

(29) The agent according to (28), wherein $R^3$ represents —$CH_2$— or —CH(OH)—$CH_2$—, and x is 10 to 32.

(30) The agent according to (29), wherein $R^3$ represents —CH(OH)—$CH_2$—.

(31) The agent according to any of (26) to (30), wherein $R^2$ and $R^4$ each represent a hydrogen atom, x is 11 to 23, and z is 0.

(32) The agent according to any of (26) to (31) for use in the treatment or prevention of diseases in which Th1/Th2 immune balance is deflected toward Th1 or diseases in which Th1 cells worsen pathological conditions.

(33) The agent according to any of (26) to (32) for use in the treatment or prevention of autoimmune diseases.

(34) The agent according to any of (26) to (32) for use in the treatment or prevention of multiple sclerosis.

Advantageous Effects of Invention

According to the present invention, the growth of T-cells producing GM-CSF can be suppressed, or their ability to produce GM-CSF can be suppressed. As a result, the amount of GM-CSF can be reduced in vivo. This probably yields a therapeutic drug for diseases caused by increase in the amount of GM-CSF.

The GM-CSF-producing T-cell control agent and the Th1/Th2 immune balance regulator of the present invention exert action and effect on humans even at a much smaller dose than a dose predicted from test results for model animals (mice, rats, and cynomolgus monkeys). Such action and effect are remarkably exerted in the case of oral administration.

DESCRIPTION OF EMBODIMENTS

1. GM-CSF-Producing T-Cell Control Agent

1-1. Summary

Figure 1:
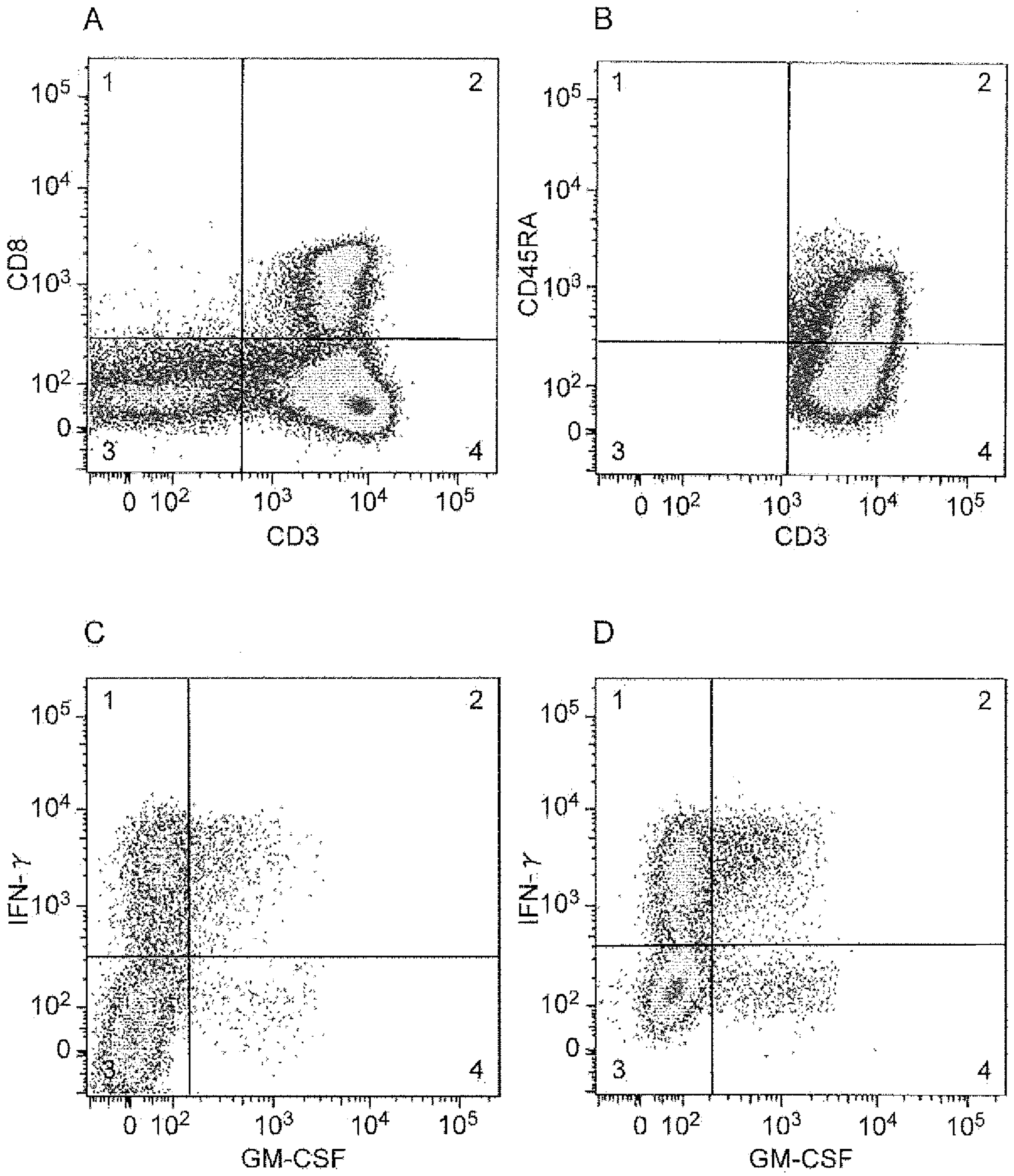
FIG. 1 is a diagram showing cytograms in which GM-CSF-producing cells in peripheral blood mononuclear cells prepared from normal subjects orally given a single dose of compound 31, which is a synthetic glycolipid of the present invention, were separated and identified by FACS. The abscissa and the ordinate of A depict the fluorescence intensity of APC-Cy7-anti-CD3 antibody and ECD-anti-CD8 antibody, respectively, at a logarithm scale. The abscissa and the ordinate of B depict the fluorescence intensity of APC-Cy7-anti-CD3 antibody and PB-anti-CD45RA antibody, respectively, at a logarithm scale. The abscissas and the ordinates of C and D depict the fluorescence intensity of PE-anti-GM-CSF antibody and PerCP-Cy5.5-anti-IFN-γ antibody, respectively, at a logarithm scale.

The first aspect of the present invention relates to a GM-CSF-producing T-cell control agent.

In the present specification, the "GM-CSF-producing T-cell control agent" refers to an agent that suppresses the growth of active T-cells having the ability to produce GM-CSF, which is an inflammatory cytokine, or suppresses their ability to produce GM-CSF. A feature of the GM-CSF-producing T-cell control agent of the present invention is to comprise the synthetic glycolipid of the present invention or a salt thereof as an active ingredient.

According to the GM-CSF-producing T-cell control agent of the present invention, it becomes possible to reduce the concentration in vivo by suppressing the growth of GM-CSF-producing T-cells.

1-2. Active Ingredient

As mentioned above, the GM-CSF-producing T-cell control agent of the present invention comprises the synthetic glycolipid of the present invention or a salt thereof as an active ingredient.

In the present specification, the "synthetic glycolipid of the present invention" means, as mentioned above, a derivative of α-galactosylceramide. Also, in this context, the "derivative of α-galactosylceramide" refers to a derivative of α-galactosylceramide (α-GalCer), as described in Japanese Patent No. 4064346, represented by the following formula (I):

[Chemical Formula 9]

(I)

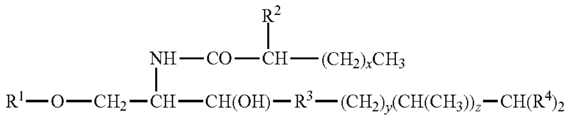

In the formula (I), $R^1$ represents an aldopyranose residue. Examples of the aldopyranose residue include α-D-glucosyl, α-D-galactosyl, α-D-mannosyl, β-D-glucosyl, β-D-galactosyl, β-D-mannosyl, 2-deoxy-2-amino-α-D-galactosyl 2-deoxy-2-amino-β-D-galactosyl, 2-deoxy-2-acetylamino-α-D-galactosyl, 2-deoxy-2-acetylamino-β-D-galactosyl, β-D-allopyranosyl, β-D-altropyranosyl, and β-D-idosyl. Among these, preferable $R^1$ is an α form. It is α-D-galactopyranosyl represented by the following formula (II):

[Chemical Formula 10]

(II)

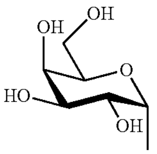

In the formula (I), $R^2$ represents a hydrogen atom (—H) or a hydroxy group (—OH). Preferred is a hydrogen atom.

In the formula (I), $R^3$ represents $—CH_2—$, $—CH(OH)—CH_2—$, or $—CH{=}CH—$. $—CH_2—$ or $—CH(OH)—CH_2—$ is more preferable, and $—CH(OH)—CH_2—$ is further preferable.

In the formula (I), $R^4$ represents a hydrogen atom (—H) or $CH_3$. Preferred is a hydrogen atom.

In the formula (I), x is an integer of 0 to 35, preferably an integer of 0 to 26, more preferably an integer of 11 to 26, further preferably an integer of 11 to 23, particularly preferably an integer of 18 to 23.

Also, in the formula (I), y and z each represent an integer that satisfies y+z=0 to 3. Preferably, z is 0, and y is 0 to 3. More preferably, z is 0, and y is 1 to 3. $—(CH_2)_y(CH(CH_3))_z—$ does not mean that the order of $(CH_2)$ and $(CH(CH_3))$ abides by the described order, and merely shows the quantitative relationship between $(CH_2)$ and $(CH(CH_3))$. For example, the case of y=2 and z=1 means that two $(CH_2)$ and one $(CH(CH_3))$ are present within $—(CH_2)_y(CH(CH_3))_z—$, and the sequence of two $(CH_2)$ and one $(CH(CH_3))$ is not limited. Specifically, it may be any of $—CH(CH_3)CH_2CH_2—$, $—CH_2CH(CH_3)CH_2—$, and $—CH_2CH_2CH(CH_3)—$.

Specific examples of the synthetic glycolipid of the present invention represented by the above formula (I) of the present invention include compounds described below in (1) to (48). Among them, the compounds of (3) to (9), (15) to (21), (27) to (33), and (39) to (45) are more preferable.

Examples thereof include (1)
(2S,3S,4R)-1-O-(α-D-galactosyl)-2-(N-triacontanoylamino)-1,3,4-heptanetriol, (2)
(2S,3S,4R)-1-O-(α-D-galactosyl)-2-(N-nonacosanoylamino)-1,3,4-heptanetriol, (3)
(2S,3S,4R)-1-O-(α-D-galactosyl)-2-(N-octacosanoylamino)-1,3,4-heptanetriol, (4)
(2S,3S,4R)-1-O-(α-D-galactosyl)-2-(N-heptacosanoylamino)-1,3,4-heptanetriol, (5)
(2S,3S,4R)-1-O-(α-D-galactosyl)-2-(N-hexacosanoylamino)-1,3,4-heptanetriol, (6)
(2S,3S,4R)-1-O-(α-D-galactosyl)-2-(N-pentacosanoylamino)-1,3,4-heptanetriol, (7)
(2S,3S,4R)-1-O-(α-D-galactosyl)-2-(N-tetracosanoylamino)-1,3,4-heptanetriol, (8)
(2S,3S,4R)-1-O-(α-D-galactosyl)-2-(N-tricosanoylamino)-1,3,4-heptane triol, (9)
(2S,3S,4R)-1-O-(α-D-galactosyl)-2-(N-docosacosanoylamino)-1,3,4-heptanetriol,

(10)
(2S,3S,4R)-1-O-(α-D-galactosyl)-2-(N-heneicosanoylamino)-1,3,4-heptanetriol,

(11)
(2S,3S,4R)-1-O-(α-D-galactosyl)-2-(N-eicosanoylamino)-1,3,4-heptanetriol,

(12)
(2S,3S,4R)-1-O-(α-D-galactosyl)-2-(N-nonadecanoylamino)-1,3,4-heptanetriol,

(13)
(2S,3S,4R)-1-O-(α-D-galactosyl)-2-(N-triacontanoylamino)-1,3,4-octanetriol,

(14)
(2S,3S,4R)-1-O-(α-D-galactosyl)-2-(N-nonacosanoylamino)-1,3,4-octanetriol,

(15)
(2S,3S,4R)-1-O-(α-D-galactosyl)-2-(N-octacosanoylamino)-1,3,4-octanetriol,

(16)
(2S,3S,4R)-1-O-(α-D-galactosyl)-2-(N-heptacosanoylamino)-1,3,4-octanetriol,

(17)
(2S,3S,4R)-1-O-(α-D-galactosyl)-2-(N-hexacosanoylamino)-1,3,4-octanetriol,

(18)
(2S,3S,4R)-1-O-(α-D-galactosyl)-2-(N-pentacosanoylamino)-1,3,4-octanetriol,

(19)
(2S,3S,4R)-1-O-(α-D-galactosyl)-2-(N-tetracosanoylamino)-1,3,4-octanetriol,
(20)
(2S,3S,4R)-1-O-(α-D-galactosyl)-2-(N-tricosanoylamino)-1,3,4-octanetriol,
(21)
(2S,3S,4R)-1-O-(α-D-galactosyl)-2-(N-docosacosanoylamino)-1,3,4-octanetriol,
(22)
(2S,3S,4R)-1-O-(α-D-galactosyl)-2-(N-heneicosanoylamino)-1,3,4-octanetriol,
(23)
(2S,3S,4R)-1-O-(α-D-galactosyl)-2-(N-eicosanoylamino)-1,3,4-octanetriol,
(24)
(2S,3S,4R)-1-O-(α-D-galactosyl)-2-(N-nonadecanoylamino)-1,3,4-octanetriol,
(25)
(2S,3S,4R)-1-O-(α-D-galactosyl)-2-(N-triacontanoylamino)-1,3,4-nonanetriol,
(26)
(2S,3S,4R)-1-O-(α-D-galactosyl)-2-(N-nonacosanoylamino)-1,3,4-nonanetriol,
(27)
(2S,3S,4R)-1-O-(α-D-galactosyl)-2-(N-octacosanoylamino)-1,3,4-nonanetriol,
(28)
(2S,3S,4R)-1-O-(α-D-galactosyl)-2-(N-heptacosanoylamino)-1,3,4-nonanetriol,
(29)
(2S,3S,4R)-1-O-(α-D-galactosyl)-2-(N-hexacosanoylamino)-1,3,4-nonanetriol,
(30)
(2S,3S,4R)-1-O-(α-D-galactosyl)-2-(N-pentacosanoylamino)-1,3,4-nonanetriol,
(31)
(2S,3S,4R)-1-O-(α-D-galactosyl)-2-(N-tetracosanoylamino)-1,3,4-nonanetriol,
(32)
(2S,3S,4R)-1-O-(α-D-galactosyl)-2-(N-tricosanoylamino)-1,3,4-nonanetriol,
(33)
(2S,3S,4R)-1-O-(α-D-galactosyl)-2-(N-docosacosanoylamino)-1,3,4-nonanetriol,
(34)
(2S,3S,4R)-1-O-(α-D-galactosyl)-2-(N-heneicosanoylamino)-1,3,4-nonanetriol,
(35)
(2S,3S,4R)-1-O-(α-D-galactosyl)-2-(N-eicosanoylamino)-1,3,4-nonanetriol,
(36)
(2S,3S,4R)-1-O-(α-D-galactosyl)-2-(N-nonadecanoyl amino)-1,3,4-nonanetriol,
(37)
(2S,3S,4R)-1-O-(α-D-galactosyl)-2-(N-triacontanoylamino)-1,3,4-hexanetriol,
(38)
(2S,3S,4R)-1-O-(α-D-galactosyl)-2-(N-nonacosanoylamino)-1,3,4-hexanetriol,
(39)
(2S,3S,4R)-1-O-(α-D-galactosyl)-2-(N-octacosanoylamino)-1,3,4-hexanetriol,
(40)
(2S,3S,4R)-1-O-(α-D-galactosyl)-2-(N-heptacosanoylamino)-1,3,4-hexanetriol,
(41)
(2S,3S,4R)-1-O-(α-D-galactosyl)-2-(N-hexacosanoylamino)-1,3,4-hexanetriol,
(42)
(2S,3S,4R)-1-O-(α-D-galactosyl)-2-(N-pentacosanoylamino)-1,3,4-hexanetriol,
(43)
(2S,3S,4R)-1-O-(α-D-galactosyl)-2-(N-tetracosanoylamino)-1,3,4-hexanetriol,
(44)
(2S,3S,4R)-1-O-(α-D-galactosyl)-2-(N-tricosanoylamino)-1,3,4-hexanetriol,
(45)
(2S,3S,4R)-1-O-(α-D-galactosyl)-2-(N-docosacosanoylamino)-1,3,4-hexanetriol,
(46)
(2S,3S,4R)-1-O-(α-D-galactosyl)-2-(N-heneicosanoylamino)-1,3,4-hexanetriol,
(47)
(2S,3S,4R)-1-O-(α-D-galactosyl)-2-(N-eicosanoylamino)-1,3,4-hexanetriol, and
(48)
(2S,3S,4R)-1-O-(α-D-galactosyl)-2-(N-nonadecanoylamino)-1,3,4-hexanetriol.

The "salt of the synthetic glycolipid of the present invention" or the "salt of the derivative of α-galactosylceramide" is a salt of the derivative of α-galactosylceramide represented by the formula (I) and refers to a salt prepared by using a base or an acid on the basis of a particular substituent on the compound. It can be classified into a base-addition salt and an acid-addition salt depending on the base or the acid used.

Examples of the base-addition salt include: alkali metal salts such as sodium salt and potassium salt; alkaline earth metal salts such as calcium salt and magnesium salt; aliphatic amine salts such as trimethylamine salt, triethylamine salt, dicyclohexylamine salt, ethanolamine salt, diethanolamine salt, triethanolamine salt, and procaine salt; aralkylamine salts such as N,N-dibenzylethylenediamine; heterocyclic aromatic amine salts such as pyridine salt, picoline salt, quinoline salt, and isoquinoline salt; basic amino acid salts such as arginine salt and lysine salt; and ammonium salts or quaternary ammonium salts such as tetramethylammonium salt, tetraethylammonium salt, benzyltrimethylammonium salt, benzyltriethylammonium salt, benzyltributylammonium salt, methyltrioctylammonium salt, and tetrabutylammonium salt.

Examples of the acid-addition salt include: inorganic acid salts such as hydrochloride, sulfate, nitrate, phosphate, carbonate, bicarbonate, and perchlorate; organic acid salts such as acetate, propionate, lactate, maleate, fumarate, tartrate, malate, citrate, and ascorbate; sulfonates such as methanesulfonate, isethionate, benzenesulfonate, and p-toluenesulfonate; and acidic amino acid salts such as aspartate and glutamate.

In the present specification, the salt of the synthetic glycolipid of the present invention also encompasses a prodrug of the synthetic glycolipid of the present invention. In this context, the "prodrug of the synthetic glycolipid of the present invention" is a compound that readily undergoes chemical change under physiological conditions and, as a result, is capable of providing the activity of suppressing the growth of GM-CSF-producing T-cells or the ability to produce GM-CSF. For example, it refers to a compound that is in a compound form different from the synthetic glycolipid of the present invention represented by the formula (I) or the base-addition salt or the acid-addition salt thereof before administration and is converted to the synthetic glycolipid of the present invention represented by the formula (I) by the action of a digestive enzyme or the like in the digestive tract.

1-3. Carrier/Solvent

The GM-CSF-producing T-cell control agent can be constituted by only the synthetic glycolipid of the present invention or the salt thereof, which is an active ingredient, but may additionally contain a pharmaceutically acceptable known and commonly used carrier and/or solvent.

The "pharmaceutically acceptable carrier" refers to a substance whose use is accepted in the field of pharmaceutical technology because of having no or very small adverse effects such as adverse reactions on animals including humans. For example, it refers to a nontoxic excipient, binder, disintegrant, filler, emulsifier, flow control additive, or the like that may be usually used in the field of pharmaceutical technology.

Examples of the excipient include sugars (e.g., but not limited to, glucose, sucrose, lactose, raffinose, mannitol, sorbitol, inositol, dextrin, maltodextrin, starch, and cellulose), metal salts (e.g., sodium chloride, sodium phosphate, calcium phosphate, calcium sulfate, magnesium sulfate, and calcium carbonate), citric acid, tartaric acid, glycine, low-, middle-, or high-molecular-weight polyethylene glycol (PEG), Pluronic, kaolin, silicic acid, and combinations thereof.

Examples of the binder include starch glues, syrups, glucose solutions, gelatin, tragacanth, methylcellulose, hydroxypropylmethylcellulose, sodium carboxymethylcellulose, shellac, and/or polyvinylpyrrolidone.

Examples of the disintegrant include starch, lactose, carboxymethyl starch, cross-linked polyvinylpyrrolidone, agar, laminaran powder, sodium bicarbonate, calcium carbonate, alginic acid or sodium alginate, polyoxyethylene sorbitan fatty acid ester, sodium lauryl sulfate, monoglyceride stearate, and salts thereof.

Examples of the filler include the sugars described above and/or calcium phosphate (e.g., tricalcium phosphate or calcium hydrogen phosphate).

Examples of the emulsifier include sorbitan fatty acid ester, glycerin fatty acid ester, sucrose fatty acid ester, and propylene glycol fatty acid ester.

Examples of the flow control additive and a lubricant include silicate, talc, stearate, and polyethylene glycol.

The pharmaceutically acceptable carrier of the present invention can also optionally include, in addition to those described above, tonicity agents, lubricants, corrigents, solubilizers, suspending agents, diluents, surfactants, stabilizers, absorption promoters (e.g., quaternary ammonium salts and sodium lauryl sulfate), expanders, pH adjusters, humectants (e.g., glycerin and starch), adsorbents (e.g., starch, lactose, kaolin, bentonite, and colloidal silicic acid), disintegration inhibitors (e.g., saccharose, stearin, cacao butter, and hydrogenated oil), coating agents, coloring agents, preservatives, antioxidants, fragrances, flavors, sweeteners, buffers, soothing agents, and the like.

The "pharmaceutically acceptable solvent" refers to a solvent whose use is accepted in the field of pharmaceutical technology because of having no or very small adverse effects such as adverse reactions on animals including humans. Examples thereof include nontoxic solvents that may be usually used in the field of pharmaceutical technology, for example, water, ethanol, propylene glycol, ethoxylated isostearyl alcohol, polyoxygenated isostearyl alcohol, and polyoxyethylene sorbitan fatty acid esters. It is preferable that these should be adjusted to be isotonic to blood.

The carrier or the solvent is mainly used for facilitating the formulation or the administration and maintaining dosage forms and pharmaceutical effects and can be appropriately used according to the need.

The GM-CSF-producing T-cell control agent of the present invention can also contain one or more agents having identical and/or different pharmacological effects within the range in which the synthetic glycolipid of the present invention or the salt thereof, which is an active ingredient, does not lose pharmacological effects, i.e., GM-CSF-producing T-cell-controlling activity. For example, in the case of the suppression of the growth of GM-CSF-producing T-cells or the suppression of the ability to produce GM-CSF according to the present invention, a predetermined amount of a gastric mucosa protecting agent can be contained according to the need.

1-4. Production Method 1-4-1. Method for Producing Synthetic Glycolipid of Present Invention, which is Active Ingredient.

The derivative of α-galactosylceramide, which is the synthetic glycolipid of the present invention, can be produced by various methods known in the art. For example, it can be produced according to a method described in Japanese Patent No. 4064346.

1-4-2. Method for Producing GM-CSF-Producing T-Cell Control Agent

As for the GM-CSF-producing T-cell control agent of the present invention, a preparation aimed at the amelioration or treatment of diseases caused by the growth of GM-CSF-producing T-cells can be prepared by utilizing the synthetic glycolipid of the present invention or the salt thereof and using a method known in the art. For example, a method described in Remington's Pharmaceutical Sciences (Merck Publishing Co., Easton, Pa.) can be used for the formulation.

The dosage form of the GM-CSF-producing T-cell control agent is appropriately selected according to an administration method and/or prescription conditions thereof. The administration method can be broadly divided into oral administration and parenteral administration.

Examples of the dosage form suitable for oral administration include tablets, pills, granules, powders, capsules, drops, sublingual formulations, troches, and solutions.

The tablets can be prepared, if necessary, as coated tablets known in the art, for example, sugar-coated tablets, gelatin-coated tablets, enteric coated tablets, film-coated tablets, bilayer tablets, or multilayer tablets. For example, the capsules can be prepared by mixing a pulverized active ingredient with an excipient such as lactose, starch or a derivative thereof, or a cellulose derivative and filling the resultant into gelatin capsules. Also, the tablets can be prepared by adding a binder such as sodium carboxymethylcellulose, alginic acid, or gum arabic, and water in addition to the excipient described above, kneading the resultant, optionally making granules, then further adding a lubricant such as talc or stearic acid, and using a usual compression tableting machine. In the case of oral administration, the shape and size of each dosage form described above can both fall within ranges known in the art and are not particularly limited.

Examples of the dosage form suitable for parenteral preparations include solutions (including suspensions), emulsions (creams), gels, ointments (including pastes), plasters, powders, and suppositories. These can be prepared as dosage forms suitable for an administration method thereof, such as systemic administration, local administration, or transrectal administration. Examples of the dosage form suitable for systemic administration include solutions as injections. In the case of injection, injection preparations are prepared by dissolving the active ingredient together with a solubilizing agent in sterile distilled water or sterile physiological saline and filling the resultant into ampules. They may optionally contain a stabilizer and a buffering substance. Examples of the dosage form suitable for local administration can include solutions as eye drops or nasal drops, emulsions, powders as nasal drops, pastes, gels, ointments, and plasters. Examples of the dosage form suitable for transrectal administration can include suppositories.

It is preferable that an effective amount of the active ingredient should be contained in the GM-CSF-producing T-cell control agent of one dosage unit. The "effective amount", when used in the present specification, refers to an amount required for the active ingredient to exert its functions, i.e., in the present invention, an amount required for the synthetic glycolipid of the present invention or the salt thereof to suppress the growth of GM-CSF-producing T-cells or the ability to produce GM-CSF, and an amount that imparts few or no adverse reactions to recipient subjects. This effective amount may vary depending on various conditions such as information on a subject, a dosage form, and an administration route. The "information on a subject" refers to the degree of progression or severity of the disease, general health conditions, age, body weight, sex, diet, drug sensitivity, the presence or absence of a concurrent drug, and resistance to treatment, etc. As a specific example of the effective amount for the GM-CSF-producing T-cell control agent, in the case of orally administering the GM-CSF-producing T-cell control agent of the present invention to a human adult man (body weight: 60 kg), one dosage unit can contain 0.01% by weight to 100% by weight, preferably 0.1% by weight to 100% by weight, of the active ingredient. Also, in the case of administering the GM-CSF-producing T-cell control agent of the present invention through an injection solution, one dosage unit of the injection solution can contain 0.01% (w/v) to 20% (w/v), preferably 0.1% (w/v) to 10% (w/v), of the active ingredient. In the case of dosage forms such as tablets, pills, or capsules, the effective amount of the GM-CSF-producing T-cells permits divided administration that is adjusted depending on the number of doses, and therefore, it is not necessarily required that the effective amount should be contained in one dosage.

1-5. Administration Method

An organism that becomes a recipient of the GM-CSF-producing T-cell control agent of the present invention is a vertebrate, preferably a mammal, more preferably a human.

A specific administration mode of the GM-CSF-producing T-cell control agent of the present invention includes, as mentioned above, oral administration or parenteral administration. The parenteral administration is further divided into systemic administration and local administration (e.g., subcutaneous administration, percutaneous administration, transmucosal administration, or transrectal administration). The administration method of the GM-CSF-producing T-cell control agent of the present invention can be appropriately selected according to the site of onset or the degree of progression of a disease, etc., and may be any of systemic administration and local administration. Preferred is low invasive oral administration. Alternatively, in the case of rapidly spreading the active ingredient via a circulatory system such as blood flow, systemic administration mediated by injection into a blood vessel is suitable. If the target disease is local, local administration for direct administration to the site of onset and its neighborhood by local injection can also be adopted. The injection site of the pharmaceutical composition by injection is not particularly limited. Examples thereof include a site within a circulatory system such as a site within a blood vessel and a site within a ventricle, and a site within an organ or a tissue such as a site within the liver, an intramuscular site, an intra-articular site, an intramedullary site, an intraspinal site, a percutaneous site, a subcutaneous site, an intraperitoneal site, an intranasal site, an intestinal site, and a sublingual site.

As one example of a specific dose, for example, in the case of administration to a human adult man (body weight: 60 kg), the dose of the GM-CSF-producing T-cell control agent per day is usually 0.001 mg to 5000 mg/day/person, preferably 0.01 mg to 500 mg/day/person, more preferably 0.01 mg to 50 mg/day/person. As shown in Examples mentioned later, the synthetic glycolipid of the present invention, which is an active ingredient, can produce adequate pharmacological effects even at a low dose. However, when the mass administration of the GM-CSF-producing T-cell control agent is necessary, the administration may be performed at several divided doses for reduction in burden on a patient.

1-5-2. Low-Dose Administration

The GM-CSF-producing T-cell control agent of the present invention exerts action and effect on humans at a much lower dose than a dose predicted from test results for model animals (mice, rats, and cynomolgus monkeys). Thus, in one embodiment, the GM-CSF-producing T-cell control agent of the present invention may be used such that 0.01 mg or larger and 50 mg or smaller of the synthetic glycolipid of the present invention (i.e., the glycolipid compound represented by the formula (I)) or the salt thereof per dosage is administered to a human. In this context, "0.01 mg or larger and 50 mg or smaller" shown as a dose means the amount of the active ingredient (i.e., the glycolipid compound represented by the formula (I) or the salt thereof) in the GM-CSF-producing T-cell control agent. This dose may be, for example, 0.05 mg or larger and 30 mg, may be 0.1 mg or larger and 30 mg or smaller, may be 0.15 mg or larger and 25 mg or smaller, may be 0.15 mg or larger and 10 mg or smaller, may be 0.2 mg or larger and 3 mg or smaller, may be 0.2 mg or larger and 1 mg or smaller, may be 0.2 mg or larger and smaller than 0.5 mg, or may be 0.2 mg or larger and 0.4 mg or smaller. As the administration method according to the present embodiment, it is preferable to be oral administration because of remarkably exerting the effects described above.

In an alternative embodiment, the GM-CSF-producing T-cell control agent of the present invention may be used such that 0.1 μg/kg body weight or larger and 1020 μg/kg body weight or smaller of the synthetic glycolipid of the present invention (i.e., the glycolipid compound represented by the formula (I)) or the salt thereof per dosage is administered to a human. This dose may be 0.7 μg/kg body weight or larger and 615 μg/kg body weight or smaller, may be 1.4 μg/kg body weight or larger and 615 μg/kg body weight or smaller, may be 2 μg/kg body weight or larger and 515 μg/kg body weight or smaller, may be 2.1 μg/kg body weight or larger and 205 μg/kg body weight or smaller, may be 2.8 μg/kg body weight or larger and 65 μg/kg body weight or smaller, may be 2.8 μg/kg body weight or larger and 25 μg/kg body weight or smaller, may be 2.8 μg/kg body weight or larger and 15 μg/kg body weight or smaller, or may be 4 μg/kg body weight or larger and 10 rig/kg body weight or smaller. In this context, for example, "4 μg/kg body weight" means that the active ingredient is 4 μg per kg of the body weight. As the administration method according to the present embodiment, it is preferable to be oral administration because of remarkably exerting the effects described above.

The invention according to each of the embodiments described above can also be regarded as a method for controlling GM-CSF-producing T-cells, comprising the step of administering the glycolipid compound represented by the formula (I) or the salt thereof in an amount of 0.01 mg to 50 mg per dosage to a human subject in need thereof. The dose may be 2 μg/kg body weight or larger and 1020 μg/kg body weight or smaller. It is preferable that the administration method should be oral administration.

In each of the embodiments described above, the dosing interval can be appropriately set according to a purpose. As the dosing interval, for example, the administration may be performed once a day, may be performed once in two days, may be performed once in three days, or may be performed once in seven days (1 week). The dosing interval for oral administration is also the same as above.

1-6. Pharmacological Effect

The GM-CSF-producing T-cell control agent of the present invention can suppress the growth of activated T-cells producing GM-CSF and suppress the ability to produce GM-CSF, by the pharmacological effects of the derivative of α-galactosylceramide or the salt thereof, which is an active ingredient.

The GM-CSF-producing T-cell-controlling effect and the concentration-lowering effect of the derivative of α-galactosylceramide or the salt thereof; which is an active ingredient in the GM-CSF-producing T-cell control agent of the present invention, is transient, and the effects are gradually weakened over time after administration. Thus, the pharmacological effects can be controlled by adjusting a dose or a dosing period.

The GM-CSF-producing T-cell control agent of the present invention can be utilized in the treatment of diseases caused by increase in GM-CSF concentration in vivo, for example, chronic inflammatory diseases such as multiple sclerosis, chronic organ inflammation, or rheumatoid arthritis, through the use of the pharmacological effects.

The invention according to each of the embodiments described above can also be regarded as a method for controlling GM-CSF-producing T-cells, comprising the step of administering an agent comprising the glycolipid compound represented by the formula (I) or the salt thereof as an active ingredient to a subject in need thereof.

The invention according to each of the embodiments described above can also be regarded as application or use of the glycolipid compound represented by the formula (I) or the salt thereof in the production of a GM-CSF-producing T-cell control agent.

1'. Agent for Use in Treatment of Diseases Caused by Increase in GM-CSF Concentration 1'-1. Summary The present invention also relates to an agent for use in the treatment of diseases caused by increase in GM-CSF concentration. The agent (composition) of the present invention for use in the treatment of diseases caused by increase in GM-CSF concentration comprises the glycolipid compound represented by the formula (I) or the salt thereof as an active ingredient.

1'-2. Active Ingredient and Carrier/Solvent

The active ingredient and the carrier/solvent of the present aspect can be the same as the active ingredient and the carrier/solvent described in the first aspect. Thus, the specific description thereof is omitted here.

1'-3. Production Method

1'-3-1. Method for Producing Active Ingredient

The synthetic glycolipid (derivative of α-galactosylceramide), which is the active ingredient of the present invention, can be produced by various methods known in the art. For example, it can be produced according to a method described in Japanese Patent No. 4064346 mentioned above.

1'-3-2. Method for Producing Agent for Use in Treatment of Diseases Caused by Increase in GM-CSF Concentration As mentioned above, the synthetic glycolipid of the present invention, which is the active ingredient of the present aspect, and the carrier/solvent can be the same as the active ingredient and the carrier/solvent described in the first aspect, and therefore, the method for producing the agent for use in the treatment of diseases caused by increase in GM-CSF concentration can also be the same as "Method for producing GM-CSF-producing T-cell control agent" described in the first aspect. Thus, the specific description thereof is omitted here.

1'-4. Administration Method

The recipient of the agent of the present invention for use in the treatment of diseases caused by increase in GM-CSF concentration is not limited as long as being a subject affected by a disease caused by increase in GM-CSF concentration. The recipient can be a vertebrate, it is preferable to be a mammal, and it is more preferable to be a human. Embodiments other than the recipient can be the same as embodiments in the GM-CSF-producing T-cell control agent described in the first aspect, as a rule. Thus, the specific description thereof is omitted here.

1'-4-2. Low-Dose Administration

An embodiment regarding the low-dose administration of the agent for use in the treatment of diseases caused by increase in GM-CSF concentration can be the same as an embodiment in the GM-CSF-producing T-cell control agent described in the first aspect, as a rule. Thus, the specific description thereof is omitted here.

1'-5. Pharmacological Effect

The agent of the present invention for use in the treatment of diseases caused by increase in GM-CSF concentration lowers the in vivo concentration in subjects affected by the diseases. This exerts therapeutic effects on the diseases caused by increase in GM-CSF concentration.

Examples of the diseases caused by increase in GM-CSF concentration include immune-mediated demyelinating disease, multiple sclerosis, chronic organ inflammation, and rheumatoid arthritis. The multiple sclerosis often develops by manifesting a single demyelinating event called CIS (clinically isolated syndrome) followed by recurrent demyelinating events. In this case, patients having CIS are diagnosed with multiple sclerosis when the demyelinating events exhibit temporal or spatial multiplicity. The agent of the present invention for use in the treatment of diseases caused by increase in GM-CSF concentration exerts therapeutic effects on immune-mediated demyelinating disease and therefore, is also effective as an agent for use in the prevention or suppression of progression from CIS to multiple sclerosis. The immune-mediated demyelinating disease means a disease that occurs by a disorder of the marrow sheath caused by immune responses.

The invention according to each of the embodiments described above can also be regarded as a method for treating diseases caused by increase in GM-CSF concentration, comprising the step of administering an agent comprising the glycolipid compound represented by the formula (I) or the salt thereof as an active ingredient to a subject in need thereof.

The invention according to each of the embodiments described above can also be regarded as application or use of the glycolipid compound represented by the formula (I) or the salt thereof in the production of an agent for use in the treatment of diseases caused by increase in GM-CSF concentration.

2. GM-CSF Lowering Agent 2-1. Summary and Definition

The second aspect of the present invention relates to a GM-CSF lowering agent.

In the present specification, the "GM-CSF lowering agent" refers to an agent having the effect of lowering the concentration in vivo. The GM-CSF lowering agent of the present invention comprises the synthetic glycolipid of the present invention or the salt thereof as an active ingredient.

2-2. Active Ingredient and Carrier/Solvent

As mentioned above, the GM-CSF lowering agent of the present invention comprises the same synthetic glycolipid of the present invention or salt thereof as in the GM-CSF-producing T-cell control agent of the first aspect as an active ingredient. Namely, the GM-CSF lowering agent of the present aspect has the same composition as in the GM-CSF-producing T-cell control agent of the first aspect. This means that the GM-CSF lowering agent of the present aspect also functions as the GM-CSF-producing T-cell control agent, and the GM-CSF-producing T-cell control agent of the first aspect can also function as the GM-CSF lowering agent of the present aspect.

Thus, the active ingredient and the carrier/solvent of the present aspect can be the same as the active ingredient and the carrier/solvent described in the first aspect, and therefore, the description thereof is omitted here.

2-3. Production Method 2-3-1. Method for Producing Active Ingredient

The synthetic glycolipid (derivative of α-galactosylceramide), which is the active ingredient of the present invention, can be produced by various methods known in the art. For example, it can be produced according to a method described in Japanese Patent No. 4064346 mentioned above.

2-3-2. Method for Producing GM-CSF Lowering Agent

As mentioned above, the synthetic glycolipid of the present invention, which is the active ingredient of the present aspect, and the carrier/solvent can be the same as the active ingredient and the carrier/solvent described in the first aspect, and therefore, the method for producing the GM-CSF lowering agent can also be the same as "Method for producing GM-CSF-producing T-cell control agent" described in the first aspect. Thus, the specific description thereof is omitted here.

2-4. Administration Method

The administration method of the GM-CSF lowering agent can also be the same as the administration method of the GM-CSF-producing T-cell control agent described in the first aspect, as a rule. Thus, the specific description thereof is omitted here.

2-4-2. Low-Dose Administration

An embodiment regarding the low-dose administration of the GM-CSF lowering agent can be the same as an embodiment in the GM-CSF-producing T-cell control agent described in the first aspect, as a rule. Thus, the specific description thereof is omitted here.

2-5. Pharmacological Effect

According to the GM-CSF lowering agent of the present invention, it becomes possible to lower the concentration in vivo.

The invention according to each of the embodiments described above can also be regarded as application or use of the glycolipid compound represented by the formula (I) or the salt thereof in the production of a GM-CSF lowering agent.

3. Th1/Th2 Immune Balance Regulator 3-1. Summary

The third aspect of the present invention relates to a Th1/Th2 immune balance regulator.

The Th1/Th2 immune balance regulator of the present invention comprises the glycolipid compound represented by the formula (I) or the salt thereof as an active ingredient. The glycolipid compound represented by the formula (I) or the salt thereof circumvents the induction of IFN-γ production and selectively induces IL-4 production. This can adjust the Th1/Th2 immune balance to a direction in which Th2 increases. The Th1/Th2 immune balance regulator of the present invention produces prophylactic effects, suppressive effects, or therapeutic effects on diseases in which Th1/Th2 immune balance is deflected toward Th1 or diseases in which Th1 cells worsen pathological conditions, via such effects. Likewise, the Th1/Th2 immune balance regulator of the present invention produces prophylactic effects, suppressive effects, or therapeutic effects on autoimmune diseases via such effects.

Thus, the Th1/Th2 immune balance regulator of the present invention can also be used as a therapeutic agent or a prophylactic agent for diseases in which Th1/Th2 immune balance is deflected toward Th1 or diseases in which Th1 cells worsen pathological conditions. Furthermore, the Th1/Th2 immune balance regulator of the present invention can also be used as a therapeutic agent or a prophylactic agent for autoimmune diseases. Moreover, the Th1/Th2 immune balance regulator of the present invention can also be used as a selective IL-4 production inducer.

The diseases in which Th1/Th2 immune balance is deflected toward Th1 or the diseases in which Th1 cells worsen pathological conditions mean diseases mainly caused by cellular immunity, such as fulminant hepatitis, graft rejection, and infectious diseases by intracellular infectious pathogens, in addition to autoimmune diseases such as immune-mediated demyelinating disease, multiple sclerosis, rheumatoid arthritis, psoriasis, type I diabetes mellitus, uveitis, and Sjogren's syndrome. The autoimmune diseases mean diseases such as immune-mediated demyelinating disease, multiple sclerosis, rheumatoid arthritis, psoriasis, Crohn disease, vitiligo vulgaris, Behcet's disease, collagen disease, type I diabetes mellitus, uveitis, Sjogren's syndrome, autoimmune myocarditis, autoimmune liver disease, autoimmune gastritis, pemphigus, Guillain-Barre syndrome, chronic inflammatory demyelinating polyneuropathy, and HTLV-1-related myelopathy. The multiple sclerosis often develops by manifesting a single demyelinating event called CIS (clinically isolated syndrome) followed by recurrent demyelinating events. In this case, patients having CIS are diagnosed with multiple sclerosis when the demyelinating events exhibit temporal or spatial multiplicity. The Th1/Th2 immune balance regulator of the present invention is also effective as an agent for use in the prevention or suppression of progression from CIS to multiple sclerosis.

3-2. Active Ingredient and Carrier/Solvent

As mentioned above, the Th1/Th2 immune balance regulator of the present invention comprises the same synthetic glycolipid of the present invention or salt thereof as in the GM-CSF-producing T-cell control agent of the first aspect as an active ingredient. Namely, the Th1/Th2 immune balance regulator of the present aspect has the same composition as in the GM-CSF-producing T-cell control agent of the first aspect.

Thus, the active ingredient and the carrier/solvent of the present aspect can be the same as the active ingredient and the carrier/solvent described in the first aspect, and therefore, the description thereof is omitted here.

3-3. Production Method 3-3-1. Method for Producing Active Ingredient

The synthetic glycolipid (derivative of α-galactosylceramide), which is the active ingredient of the present invention, can be produced by various methods known in the art. For example, it can be produced according to a method described in Japanese Patent No. 4064346 mentioned above.

3-3-2. Method for Producing Th1/Th2 Immune Balance Regulator

As mentioned above, the synthetic glycolipid of the present invention, which is the active ingredient of the present aspect, and the carrier/solvent can be the same as the active ingredient and the carrier/solvent described in the first aspect, and therefore, the method for producing the Th1/Th2 immune balance regulator can also be the same as "Method for producing GM-CSF-producing T-cell control agent" described in the first aspect. Thus, the specific description thereof is omitted here.

3-4. Administration Method (Low-Dose Administration)

An organism that becomes a recipient of the Th1/Th2 immune balance regulator of the present invention is a vertebrate, preferably a mammal, more preferably a human.

A specific administration mode of the Th1/Th2 immune balance regulator of the present invention includes, as mentioned above, oral administration or parenteral administration. The parenteral administration is further divided into systemic administration and local administration (e.g., subcutaneous administration, percutaneous administration, transmucosal administration, or transrectal administration). The administration method of the Th1/Th2 immune balance regulator of the present invention can be appropriately selected according to a site for which the regulation of Th1/Th2 immune balance is necessary, the site of onset or the degree of progression of an autoimmune disease or the like, etc., and may be any of systemic administration and local administration. Preferred is low invasive oral administration. Alternatively, in the case of rapidly spreading the active ingredient via a circulatory system such as blood flow, systemic administration mediated by injection into a blood vessel is suitable. If the target disease or the like is local, local administration for direct administration to the site of onset and its neighborhood by local injection can also be adopted. The injection site of the pharmaceutical composition by injection is not particularly limited. Examples thereof include a site within a circulatory system such as a site within a blood vessel and a site within a ventricle, and a site within an organ or a tissue such as a site within the liver, an intramuscular site, an intra-articular site, an intramedullary site, an intraspinal site, a percutaneous site, a subcutaneous site, an intraperitoneal site, an intranasal site, an intestinal site, and a sublingual site.

The Th1/Th2 immune balance regulator of the present invention exerts action and effect on humans at a much lower dose than a dose predicted from test results for model animals (mice, rats, and cynomolgus monkeys). Thus, in one embodiment, the Th1/Th2 immune balance regulator of the present invention may be used such that 0.01 mg or larger and 50 mg or smaller of the synthetic glycolipid of the present invention (i.e., the glycolipid compound represented by the formula (I)) or the salt thereof per dosage is administered to a human. In this context, "0.01 mg or larger and 50 mg or smaller" shown as a dose means the amount of the active ingredient (i.e., the glycolipid compound represented by the formula (I) or the salt thereof) in the Th1/Th2 immune balance regulator. This dose may be, for example, 0.05 mg or larger and 30 mg, may be 0.1 mg or larger and 30 mg or smaller, may be 0.15 mg or larger and 25 mg or smaller, may be 0.15 mg or larger and 10 mg or smaller, may be 0.2 mg or larger and 3 mg or smaller, may be 0.2 mg or larger and 1 mg or smaller, may be 0.2 mg or larger and smaller than 0.5 mg, or may be 0.2 mg or larger and 0.4 mg or smaller. As the administration method according to the present embodiment, it is preferable to be oral administration because of remarkably exerting the effects described above.

In an alternative embodiment, the Th1/Th2 immune balance regulator of the present invention may be used such that 0.1 μg/kg body weight or larger and 1020 μg/kg body weight or smaller of the synthetic glycolipid of the present invention (i.e., the glycolipid compound represented by the formula (I)) or the salt thereof per dosage is administered to a human. This dose may be 0.7 μg/kg body weight or larger and 615 μg/kg body weight or smaller, may be 1.4 μg/kg body weight or larger and 615 μg/kg body weight or smaller, may be 2 μg/kg body weight or larger and 515 μg/kg body weight or smaller, may be 2.1 μg/kg body weight or larger and 205 μg/kg body weight or smaller, may be 2.8 μg/kg body weight or larger and 65 μg/kg body weight or smaller, may be 2.8 μg/kg body weight or larger and 25 μg/kg body weight or smaller, may be 2.8 μg/kg body weight or larger and 15 μg/kg body weight or smaller, or may be 4 μg/kg body weight or larger and 10 μg/kg body weight or smaller. In this context, for example, "4 μg/kg body weight" means that the active ingredient is 4 μg per kg of the body weight. As the administration method according to the present embodiment, it is preferable to be oral administration because of remarkably exerting the effects described above.

The invention according to each of the embodiments described above can also be regarded as a method for regulating Th1/Th2 immune balance, comprising the step of administering the glycolipid compound represented by the formula (I) or the salt thereof in an amount of 0.01 mg to 50 mg per dosage to a human subject in need thereof. Furthermore, the invention according to each of the embodiments described above can also be regarded as a method for treating or a method for preventing diseases in which Th1/Th2 immune balance is deflected toward Th1 or diseases in which Th1 cells worsen pathological conditions, comprising the step of administering the glycolipid compound represented by the formula (I) or the salt thereof in an amount of 0.01 mg to 50 mg per dosage to a human subject in need thereof. Moreover, the invention according to each of the embodiments described above can also be regarded as a method for treating or a method for preventing autoimmune diseases, comprising the step of administering the glycolipid compound represented by the formula (I) or the salt thereof in an amount of 0.01 mg to 50 mg per dosage to a human subject in need thereof. The dose may be 2 μg/kg body weight or larger and 1020 μg/kg body weight or smaller. It is preferable that the administration method should be oral administration.

In each of the embodiments described above, the dosing interval can be appropriately set according to a purpose. As the dosing interval, for example, the administration may be performed once a day, may be performed once in two days, may be performed once in three days, or may be performed once in seven days (1 week).

3-5. Pharmacological Effect

The Th1/Th2 immune balance regulator of the present invention circumvents the induction of IFN-γ production and selectively induces IL-4 production by administration to a human. As a result, the Th1/Th2 immune balance is shifted to a direction in which Th2 increases, and the suppression of Th1 cellular immune responses takes place so that therapeutic effects or prophylactic effects on autoimmune diseases and therapeutic effects or prophylactic effects on diseases in which Th1/Th2 immune balance is deflected toward Th1 or diseases in which Th1 cells worsen pathological conditions are exerted.

The invention according to each of the embodiments described above can also be regarded as application or use of the glycolipid compound represented by the formula (I) or the salt thereof in the production of a Th1/Th2 immune balance regulator.

The invention according to each of the embodiments described above can also be regarded as an agent (composition) for use in the treatment or prevention of diseases in which Th1/Th2 immune balance is deflected toward Th1 or diseases in which Th1 cells worsen pathological conditions.

EXAMPLES

Example 1: Suppression of GM-CSF-Producing T-Cell by Synthetic Glycolipid of Present Invention

Objective

Suppressive effects on GM-CSF-producing T-cells by the administration of the synthetic glycolipid of the present invention were verified.

Method (1) Administration of Synthetic Glycolipid of Present Invention to Normal Subject

TABLE 1

| Cohort | No. | Age | Sex | Height (cm) | Body weight (kg) |
|---|---|---|---|---|---|
| A | A-1 | 42 | Male | 178.0 | 70.6 |
| | A-3 | 29 | Male | 174.2 | 57.9 |
| | A-4 | 29 | Male | 171.5 | 64.2 |
| B | B-1 | 23 | Male | 171.5 | 57.5 |
| | B-3 | 36 | Male | 183.0 | 66.2 |
| | B-4 | 26 | Male | 177.5 | 69.0 |
| C | C-1 | 22 | Male | 172.7 | 58.9 |
| | C-2 | 36 | Male | 169.5 | 66.8 |
| | C-3 | 20 | Male | 171.8 | 54.8 |
| D | D-1 | 21 | Male | 170.5 | 54.8 |
| | D-3 | 22 | Male | 170.5 | 70.8 |
| | D-4 | 21 | Female | 159.9 | 48.9 |

A single dose of compound 31, which is a synthetic glycolipid of the present invention, described in the first aspect, i.e., (2S,3S,4R)-1-O-(α-D-galactosyl)-2-(N-tetracosanoylamino)-1,3,4-nonanetriol represented by the following formula (III), was orally administered to each of subjects of 4 cohorts (A, B, C, and D cohorts) each consisting of 3 normal subjects shown in Table 1 above after obtainment of informed consent.

[Chemical Formula 11]

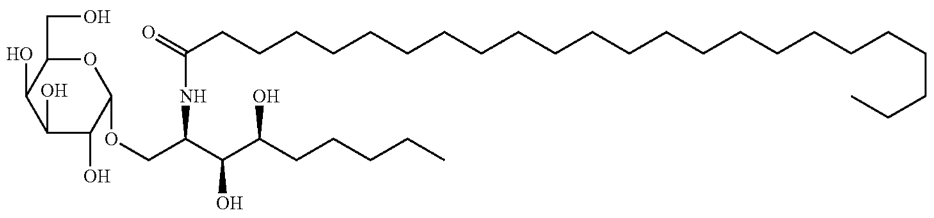

(III)

The dose was set to 0.3 mg per person for A cohort, 1 mg per person for B cohort, 3 mg per person for C cohort, and 10 mg per person for D cohort.

(2) Preparation of Peripheral Blood Mononuclear Cell (PBMC)

Subsequently, T-cell subfractions were prepared from the peripheral blood of each subject by using the density gradient centrifugation method. First, a total of 20 mL of blood was collected from the vein of each subject 24 hours (1st day), 48 hours (2nd day), 72 hours (3rd day), and 168 hours (7th day) after the administration of compound 31 by using two 10-mL heparin sodium-containing vacuum blood collection tubes. For a control, 20 mL of blood was similarly collected from the vein of each subject one day before the administration of compound 31.

Next, 4 mL of Ficoll-Paque Plus (GE Healthcare Biosciences Corp.) was placed in each of four 15-mL conical tubes, and 10 mL of blood diluted twice with phosphate buffered saline (PBS) was gently layered thereon. Then, density gradient centrifugation was performed by centrifugation at 1800 rpm at ordinary temperature for 30 minutes. After the centrifugation, a supernatant containing plasma and platelet was discarded, and lymphocytes present at the boundary layer between the supernatant layer and the Ficoll-Paque Plus layer were recovered into a fresh 50-mL conical tube. The 50-mL conical tube was filled by adding PBS thereto, followed by centrifugation at 1800 rpm at ordinary temperature for 5 minutes. After a supernatant was removed by suction, PBS was added and pipetting was performed, the resultant was transferred to a fresh 15-mL conical tube while passed through BD Falcon Cell Strainer (Becton, Dickinson and Company) having a diameter of 40 μm, followed by centrifugation at 1500 rpm for 5 minutes. After a supernatant was removed by suction again, a single cell suspension was prepared by adding 1 mL of AIM-V medium (Life Technologies Corp.), and then, the number of cells was measured with a counting chamber. The single cell suspension including $5\times10^5$ cells/well of the cells was inoculated to 4 wells of BD Falcon 96-well flat bottom plate (Becton, Dickinson and Company). The cells were stimulated by adding PMA (Sigma-Aldrich Corp.), ionomycin (Sigma-Aldrich Corp.), and monensin (Sigma-Aldrich Corp.) to each well such that the final concentrations became 50 ng/mL, 500 ng/mL, and 2 μM, respectively. Subsequently, the cells of the 4 wells, after being cultured at 37° C. for 4 hours in a 5% $CO_2$ incubator, were collected into each of flow cytometry tubes, manufactured by Becton, Dickinson and Company. After centrifugation at 1500 rpm at ordinary temperature for 5 minutes, a supernatant was removed by suction, and peripheral blood mononuclear cells (PBMCs) were collected.

(3) Antibody Staining and Flow Cytometry

The collected PBMCs were stained with antibodies by the following method. First, 10 μL of a solution consisting of 8 μL of PBS containing 0.5% BSA/2 mM EDTA-2Na, 0.5 μL of APC-Cy7-anti-CD3 antibody (BioLegend, Inc.), 0.5 μL of ECD-anti-CD8 antibody (Beckman Coulter, Inc.), and 1 μL of PB-anti-CD45RA antibody (BioLegend, Inc.) was added to $2\times10^6$ cells of PBMCs, thoroughly mixed by vortexing, and then left on ice for 10 minutes. CD3 is a detection marker of T-cells, and $CD3^+$ cells mean being T-cells. Also, CD45RA is a detection marker of naive T-cells, and $CD45RA^+$ cells mean being naive T-cells. Also, $CD45RA^-$ cells mean being memory T-cells. Furthermore, $CD8^-$ cells mean being $CD4^+$ cells. 1 mL of PBS containing 0.5% BSA/2 mM EDTA-2Na was added, and after centrifugation at 1500 rpm for 5 minutes, a supernatant was removed by suction. Next, 100 μL of BD FIX buffer (Becton, Dickinson and Company) was added dropwise while vortexed, and then left on ice for 20 minutes. 1 mL of MACS buffer was added again, and after centrifugation at 1500 rpm for 5 minutes, a supernatant was removed by suction. Subsequently, 1 mL of 0.1% saponin was added, and the resultant was left at room temperature under light shielding for 2 minutes.

Subsequently, the resultant was dispensed as 250 μL (group I) and 750 μL (group II), and after centrifugation at 2200 rpm for 5 minutes, a supernatant was removed by suction.

For group I, 11 μL of a solution consisting of 7 μL of 0.1% saponin, 1 μL of PerCP-Cy5.5-anti-mouse IgG1 antibody (BioLegend, Inc.), 1 μL of Alexa 488-anti-mouse IgG1 antibody (BioLegend, Inc.), 1 μL of APC-anti-mouse IgG1 antibody (BioLegend, Inc.), and 1 μL of PE-anti-rat IgG1 antibody (Becton, Dickinson and Company) was added, thoroughly mixed by vortexing, and then left on ice for 10 minutes. 1 mL of 0.1% saponin was added, and after centrifugation at 2200 rpm for 5 minutes, a supernatant was removed by suction. After 300 μL of MACS buffer was added, centrifugation was performed at 2200 rpm for 5 minutes. 350 μL of PBS containing 0.5% BSA/2 mM EDTA-2Na was added, and the resultant was passed through BD Falcon Cell Strainer (Becton, Dickinson and Company). The obtained cells were used as “lymphocyte cells for control”.

For group II, 12 μL of a solution consisting of 7 μL of 0.1% saponin, PerCP-Cy5.5-anti-IFN-γ antibody (BioLegend, Inc.), 3 μL of Alexa 488-anti-IL-17 antibody (BioLegend, Inc.), and 1 μL of APC-anti-IL-4 antibody (BioLegend, Inc.) was added, thoroughly mixed by vortexing, and then left on ice for 10 minutes. After the total amount was adjusted to 32 μL by adding 20 μL of 0.1% saponin, 10 μL was isolated and adjusted to 15 μL by adding 5 μL PE-anti-GM-CSF antibody (BioLegend, Inc.), then thoroughly mixed by vortexing, and then left on ice for 10 minutes. 1 mL of 0.1% saponin was added, and after centrifugation at 2200 rpm for 5 minutes, a supernatant was removed by suction. Subsequently, after 300 μL of PBS containing 0.5% BSA/2 mM EDTA-2Na was added, centrifugation was performed at 2200 rpm for 5 minutes, 350 μL of PBS containing 0.5% BSA/2 μM EDTA-2Na was added, and the resultant was passed through BD Falcon Cell Strainer (Becton, Dickinson and Company). The obtained cells were used as “lymphocyte cells”.

On the basis of the fluorescent labels of each antibody-stained lymphocyte cell, each cell was separated and identified with FACS Aria II (Becton, Dickinson and Company). The cytograms obtained by FACS are shown in FIG. 1. On the basis of the fluorescence intensity of each antibody, cytograms A to D were each fractionated into 4 zones (1 to 4). A2 zone is $CD3^+CD8^+$ cell zone, and A4 zone is $CD3^+CD8^-$ cell zone.

A cytogram in which the $CD3^+CD8^+$ cells in A2 zone were refractionated by FACS on the basis of the fluorescence of PerCP-Cy5.5-anti-IFN-γ antibody and PE-anti-GM-CSF antibody is C, and the cells of C2/C4 zone are the GM-CSF-producing CD8-positive T-cell fraction of interest.

On the other hand, a cytogram in which the $CD3^+CD8^-$ cells in A4 zone were refractionated by FACS on the basis of the fluorescence of APC-Cy7-anti-CD3 antibody and PB-anti-CD45RA antibody is B, and $CD3^+CD8^-CD45RA^-$ B4 zone is a CD4-positive memory T-cell fraction. A cytogram in which this fraction was further refractionated by FACS on the basis of the fluorescence of PerCP-Cy5.5-anti-IFN-γ antibody and PE-anti-GM-CSF antibody is D, and the cells of D2/D4 zone are the GM-CSF-producing CD4-positive memory T-cell fraction of interest.

The abundance ratio (%) in the measured PBMCs was calculated as to the cells contained in each of the GM-CSF-producing CD4-positive memory T-cell fraction and the GM-CSF-producing CD8-positive T-cell fraction.

Results

Figure 2:
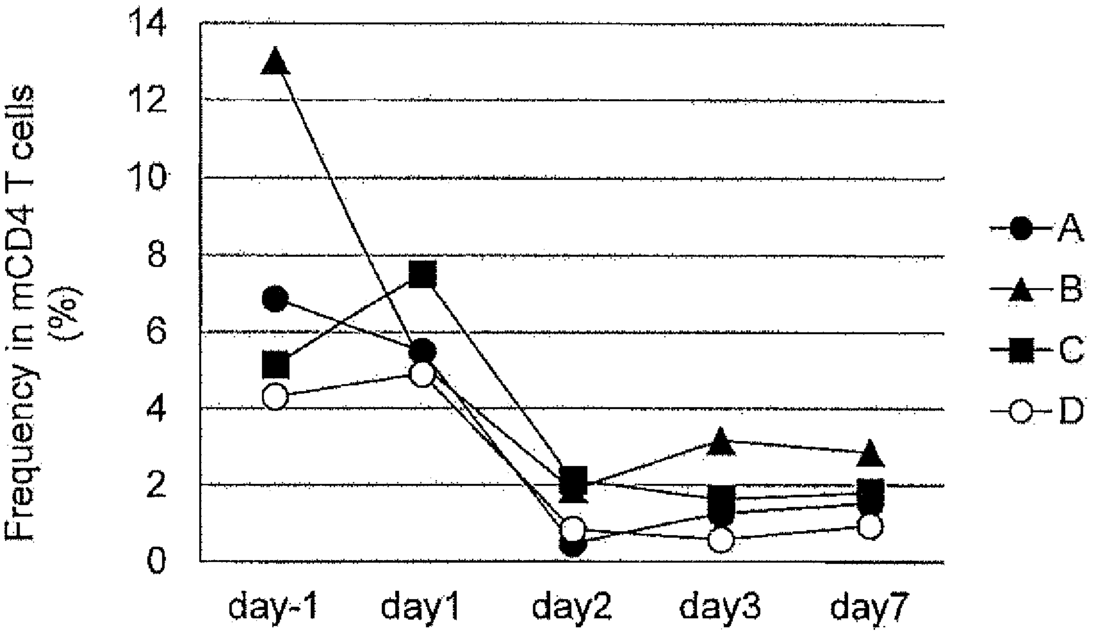
FIG. 2 is a diagram showing time-dependent change in the ratio of GM-CSF-producing CD4-positive memory T-cells to peripheral blood mononuclear cells prepared from normal subjects orally given a single dose of compound 31, which is a synthetic glycolipid of the present invention. In the diagram, A to D represent cohort A (0.3 mg administration), cohort B (1 mg administration), cohort C (3 mg administration), and cohort D (10 mg administration). Also, day-1 represents one day before the administration of compound 31, and day1, day2, day3, and day7 represent one day, two days, three days, and seven days, respectively, after the administration of compound 31.
Figure 3:
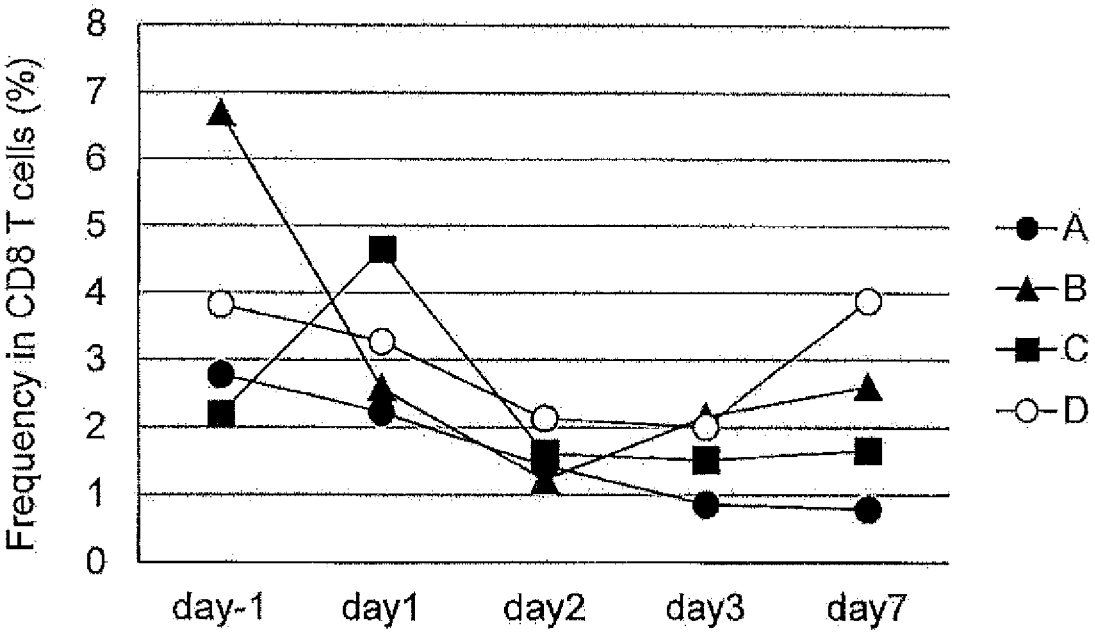
FIG. 3 is a diagram showing time-dependent change in the ratio of GM-CSF-producing CD8-positive T-cells to peripheral blood mononuclear cells prepared from normal subjects orally given a single dose of compound 31, which is a synthetic glycolipid of the present invention. In the diagram, A to D represent cohort A (0.3 mg administration), cohort B (1 mg administration), cohort C (3 mg administration), and cohort D (10 mg administration). Also, day-1 represents one day before the administration of compound 31, and day1, day2, day3, and day7 represent one day, two days, three days, and seven days, respectively, after the administration of compound 31.

The results about the abundance ratio of the GM-CSF-producing CD4-positive memory T-cells in PBMCs are shown in FIG. 2, and the results about the abundance ratio of the GM-CSF-producing CD8-positive T-cells in PBMCs are shown in FIG. 3.

A to D in FIGS. 2 and 3 each denote an average value of proportions of CD4-positive memory T-cells (FIG. 2) and an average value of proportions of CD8-positive T-cells (FIG. 3) in PBMCs of the 3 subjects constituting each cohort.

In FIG. 2, the proportion of GM-CSF-producing CD4-positive memory T-cells decreased for all of the cohorts after the administration of compound 31 as compared with the compound 31 pre-administration value (day-1), indicating that the growth of CD4-positive memory T-cells was suppressed or their ability to produce GM-CSF was suppressed by the administration of compound 31. Also, from the results about A cohort, it was revealed that compound 31 has high suppressive effects on CD4-positive memory T-cells even at a low dose.

It was also found that when the dose of compound 31 was large (C and D cohorts), the growth of GM-CSF-producing CD4-positive memory T-cells was promoted 1 day after the administration of compound 31, though the effects were transient and strongly suppressed on the next day in both cases.

It was also revealed that when a single dose of compound 31 was administered, the suppressive effects reached a peak 48 hours (day2) to 72 hours (day3) after the administration of compound 31 for all of the cohorts, and thereafter, CD4-positive memory T-cells gradually begun a recovery process. This suggests that the suppressive effects of compound 31 on CD4-positive memory T-cells are sustained for a few days, but are not permanent, and suggests that the suppressive effects of compound 31 on CD4-positive memory T-cells can be controlled by a dose or a dosing period.

Meanwhile, the basic tendency of FIG. 3 was also similar to that of FIG. 2. Namely, the proportion of CD8-positive T-cells decreased for all of the cohorts after the administration of compound 31 as compared with that before the administration of the compound 31 (day-1). Also, when the dose of compound 31 was large, the growth of CD8-positive T-cells was transiently promoted 1 day after the administration of compound 31 (C cohort). Furthermore, it was also revealed that when a single dose of compound 31 was administered, the suppressive effects reached a peak 48 hours (day2) to 72 hours (day3) after the administration of compound 31 for B to D cohorts, and the cells gradually begun a recovery process. However, the suppressive effects were strengthened even 7 days after the administration for A cohort to which the dose was smallest.

Example 2: Influence of Compound 31 on GM-CSF Production by Mouse T-Cell

Objective

It was verified that the results observed in the normal subjects of Example 1 were also reproducible for mice. Because it is difficult to analyze peripheral blood of mice, the amount of GM-CSF in lymph node cell culture supernatants of mice given compound 31 was analyzed as the ability of lymph node cells to produce GM-CSF.

Method (1) Administration of Synthetic Glycolipid of Present Invention to Mouse Compound 31 was orally administered to 8-week-old C57BL/6 mice (female) by using a probe. The dose employed 15 μg/kg (low dose) of compound 31 or 1 mg/kg (high dose) of compound 31 dissolved in 200 μL of mouse drinking water. As a control, 200 μL of mouse drinking water was administered alone.

(2) Preparation of Lymph Node Cell 2 days or 7 days after the oral administration of compound 31, each mouse was euthanized by cervical dislocation, and axillary and inguinal lymph nodes were collected. The collected lymph nodes were disrupted on BD Falcon Cell Strainer (Becton, Dickinson and Company) having a diameter of 40 μm, PBS was added, and the resultant was recovered into a 50-mL conical tube and centrifuged at 1500 rpm for 5 minutes, and then, a supernatant was removed by suction.

The recovered cells were suspended into a single cell suspension by adding 1000 μL of an RPMI medium (Life Technologies Corp.) containing 10% FBS (Fetal Bovine Serum; Life Technologies Corp.), and then, the number of cells was measured with a counting chamber.

(3) Antibody Stimulation and Detection of GM-CSF in Culture Supernatant

On the day prior to the lymph node collection from the mice after the administration, an anti-CD3 monoclonal antibody (self-produced) and an anti-CD28 antibody (Becton, Dickinson and Company) were each adjusted to 1 μg/mL with PBS, placed at 50 μL to each well of BD Falcon 96-well flat bottom plate (Becton, Dickinson and Company), and stored at 4° C. so that the plate was coated with the anti-CD3/CD28 antibodies. The prepared single cell suspension was inoculated at $5\times10^5$ cells/well to the plate and then cultured at 37° C. for 48 hours in a 5% $CO_2$ incubator to perform stimulation with the anti-CD3 antibody and the anti-CD28 antibody.

A supernatant was recovered, and the concentration of GM-CS contained in the culture supernatant was measured by using an ELISA kit (OptEIA Mouse GM-CSF ELISA set; Becton, Dickinson and Company) according to the attached document.

Results

Figure 4:
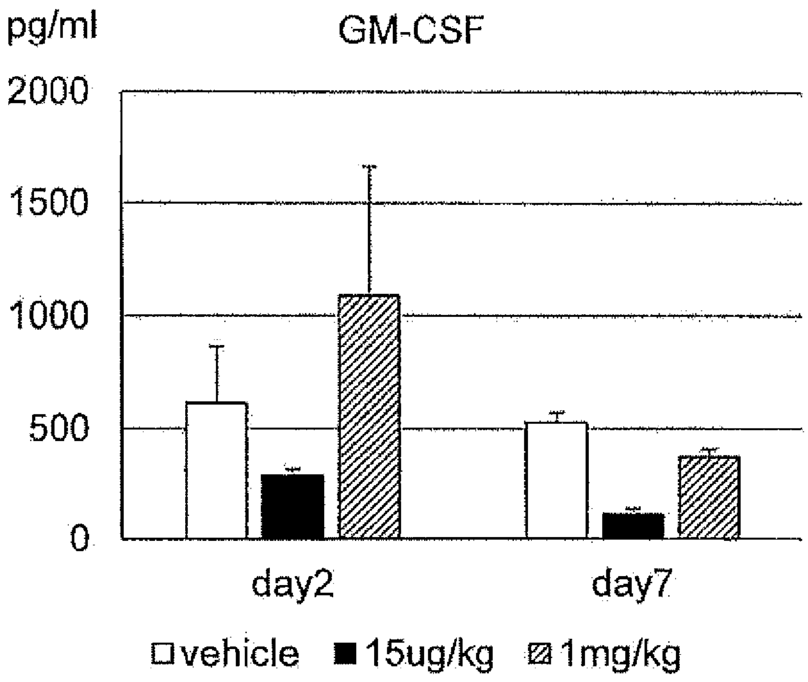
FIG. 4 is a diagram showing the amount of GM-CSF in lymph node cell culture supernatants of mice orally given a single dose of compound 31, which is a synthetic glycolipid of the present invention. day2 and day7 represent the culture supernatants of lymph node cells collected from the mice 2 days and 7 days, respectively, after the administration of compound 31. vehicle is a control given water (mouse drinking water) alone instead of the administration of compound 31.

The results are shown in FIG. 4. It was found that GM-CSF production from lymph node T-cells was significantly suppressed in the low-dose administration (15 μg/kg) of compound 31. On the other hand, in the high-dose group (1 mg/kg), the suppressive effects were not seen on the 2nd day after the administration of compound 31, but were observed on the 7th day after the administration. Thus, it was shown that although the time when the effects of compound 31 start to appear differs among doses, eventually, GM-CSF production from lymph node T-cells is significantly suppressed. This suggests that tendency similar to the results of Examples 1 and 2 using human peripheral blood was also reproducible for mice. The amount of GM-CSF in the culture supernatant of lymph node T-cells decreased by the administration of compound 31, demonstrating that the in vivo suppression of GM-CSF-producing T-cells brings about the effect of lowering the in vivo concentration.

Example 3: Suppression of GM-CSF-Producing T-Cell in MS Patient

Objective

Suppressive effects on GM-CSF-producing T-cells by the administration of the synthetic glycolipid of the present invention were verified in patients having multiple sclerosis (MS patients).

Method (1) Administration of Synthetic Glycolipid of Present Invention to MS Patient

TABLE 2

| No. | Age | Sex | Height (cm) | Body weight (kg) |
|---|---|---|---|---|
| 1 | 29 | Female | 151.5 | 71.0 |
| 2 | 34 | Male | 179.8 | 67.0 |

A single dose of compound 31, which is a synthetic glycolipid of the present invention, described in the first aspect was orally administered to each of 2 MS patients (subjects) shown in Table 2 above after obtainment of informed consent. The dose was set to 0.3 mg per person.

(2) Preparation of Peripheral Blood Mononuclear Cell (PBMC)

Subsequently, T-cell subfractions were prepared from the peripheral blood of each subject by using the density gradient centrifugation method. First, a total of 20 mL of blood was collected from the vein of each subject 24 hours (1st day), 48 hours (2nd day), 72 hours (3rd day), 168 hours (7th day), and 192 hours (8th day) after the administration of compound 31 by using two 10-mL heparin sodium-containing vacuum blood collection tubes. For a control, 20 mL of blood was similarly collected from the vein of each subject one day before the administration of compound 31.

Hereinafter, peripheral blood mononuclear cells (PBMCs) were collected by the same operation as in Example 1.

(3) Antibody Staining and Flow Cytometry

The collected PBMCs were stained with antibodies by the following method. First, 10 μL of a solution consisting of 8 μL of PBS containing 0.5% BSA/2 mM EDTA-2Na, 0.5 μL of APC-Cy7-anti-CD3 antibody (BioLegend, Inc.), 0.5 μL of ECD-anti-CD8 antibody (Beckman Coulter, Inc.), and 1 μL of PB-anti-CD45RA antibody (BioLegend, Inc.) was added to $2\times10^6$ cells of PBMCs, thoroughly mixed by vortexing, and then left on ice for 10 minutes. CD3 is a detection marker of T-cells, and $CD3^+$ cells indicate being T-cells. Also, CD45RA is a detection marker of naive T-cells, and $CD45RA^+$ cells indicate being naive T-cells. Also, $CD45RA^-$ cells indicate being memory T-cells. Furthermore, $CD8^-$ cells indicate being $CD4^+$ cells. 1 mL of PBS containing 0.5% BSA/2 mM EDTA-2Na was added, and after centrifugation at 1500 rpm for 5 minutes, a supernatant was removed by suction. Next, 100 μL of BD FIX buffer (Becton, Dickinson and Company) was added dropwise while vortexed, and then left on ice for 20 minutes. 1 mL of MACS buffer was added again, and after centrifugation at 1500 rpm for 5 minutes, a supernatant was removed by suction. Subsequently, 1 mL of 0.1% saponin was added, and the resultant was left at room temperature under light shielding for 2 minutes.

Subsequently, the resultant was dispensed as 250 μL (I group) and 750 μL (II group), and after centrifugation at 2200 rpm for 5 minutes, a supernatant was removed by suction.

For group I, 11 μL of a solution consisting of 7 μL of 0.1% saponin, 1 μL of PerCP-Cy5.5-anti-mouse IgG1 antibody (BioLegend, Inc.), 1 μL of Alexa 488-anti-mouse IgG1 antibody (BioLegend, Inc.), 1 μL of APC-anti-mouse IgG1 antibody (BioLegend, Inc.), and 1 μL of PE-anti-rat IgG1 antibody (Becton, Dickinson and Company) was added, thoroughly mixed by vortexing, and then left on ice for 10 minutes. 1 mL of 0.1% saponin was added, and after centrifugation at 2200 rpm for 5 minutes, a supernatant was removed by suction. After 300 μL of MACS buffer was added, centrifugation was performed at 2200 rpm for 5 minutes. 350 μL of PBS containing 0.5% BSA/2 mM EDTA-2Na was added, and the resultant was passed through BD Falcon Cell Strainer (Becton, Dickinson and Company). The obtained cells were used as “lymphocyte cells for control”.

For group II, 12 μL of a solution consisting of 7 μL of 0.1% saponin, PerCP-Cy5.5-anti-IFN-γ antibody (BioLegend, Inc.), 3 μL of Alexa 488-anti-IL-17 antibody (BioLegend, Inc.), and 1 μL of APC-anti-IL-4 antibody (BioLegend, Inc.) was added, thoroughly mixed by vortexing, and then left on ice for 10 minutes. After the total amount was adjusted to 32 μL by adding 20 μL of 0.1% saponin, 10 μL was isolated and adjusted to 15 μL by adding 5 μL PE-anti-GM-CSF antibody (BioLegend, Inc.), then thoroughly mixed by vortexing, and then left on ice for 10 minutes. 1 mL of 0.1% saponin was added, and after centrifugation at 2200 rpm for 5 minutes, a supernatant was removed by suction. Subsequently, after 300 μL of PBS containing 0.5% BSA/2 mM EDTA-2Na was added, centrifugation was performed at 2200 rpm for 5 minutes, 350 μL of PBS containing 0.5% BSA/2 μM EDTA-2Na was added, and the resultant was passed through BD Falcon Cell Strainer (Becton, Dickinson and Company). The obtained cells were used as “lymphocyte cells”.

On the basis of the fluorescent labels of each antibody-stained lymphocyte cell, each cell was separated and identified with FACS Aria II (Becton, Dickinson and Company). The cytograms obtained by FACS are shown in FIG. 1. On the basis of the fluorescence intensity of each antibody, cytograms A to D were each fractionated into 4 zones (1 to 4). A2 zone is $CD3^+CD8^+$ cell zone, and A4 zone is $CD3^+CD8^-$ cell zone.

A cytogram in which the $CD3^+CD8^-$ cells in A4 zone were refractionated by FACS on the basis of the fluorescence of APC-Cy7-anti-CD3 antibody and PB-anti-CD45RA antibody is B, and B4 zone of $CD3^+CD8^-CD45RA^-$ is a CD4-positive memory T-cell fraction. A cytogram in which this fraction was further refractionated by FACS on the basis of the fluorescence of PerCP-Cy5.5-anti-IFN-γ antibody and PE-anti-GM-CSF antibody is D, and the cells of D2/D4 zone are the GM-CSF-producing CD4-positive memory T-cell fraction of interest.

The abundance ratio (%) in the measured PBMCs was calculated as to the cells contained in each of the GM-CSF-producing CD4-positive memory T-cell fraction and the GM-CSF-producing CD8-positive T-cell fraction.

Results

Figure 5:
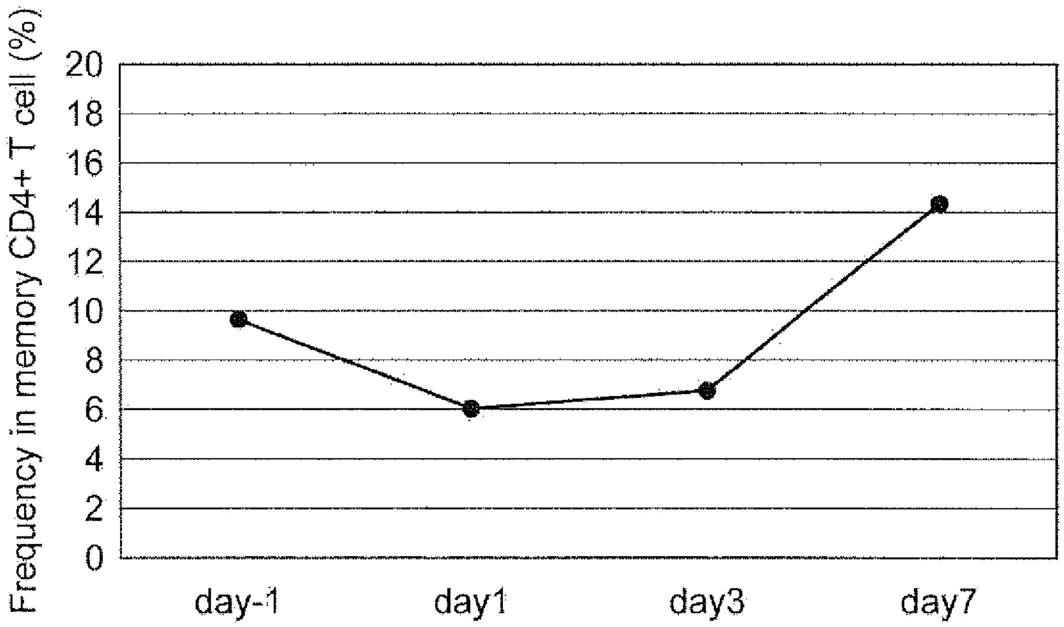
FIG. 5 is a diagram showing time-dependent change in the ratio of GM-CSF-producing CD4-positive memory T-cells to peripheral blood mononuclear cells prepared from MS patients orally given a single dose of compound 31 (0.3 mg administration), which is a synthetic glycolipid of the present invention. Also, day-1 represents one day before the administration of compound 31, and day1, day3, and day7 represent one day, three days, and seven days, respectively, after the administration of compound 31.
Figure 6:
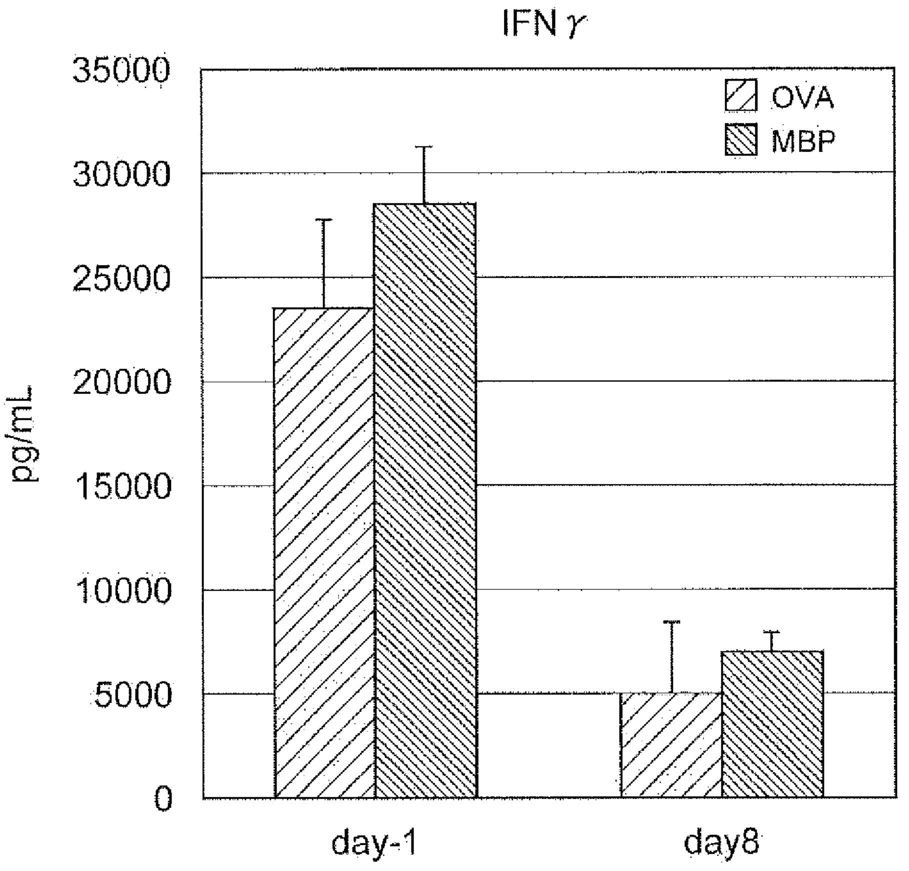
FIG. 6 is a diagram showing change in IFN-γ expression level in a CD4-positive memory T-cell fraction ($CD3^+CD4^+CD45RA^-$) recovered by cell sorting from peripheral blood mononuclear cells prepared from MS patients orally given a single dose of compound 31 (0.3 mg administration), which is a synthetic glycolipid of the present invention. Also, day-1 represents one day before the administration of compound 31, and day8 represents 8 days after the administration of compound 31.
Figure 7:
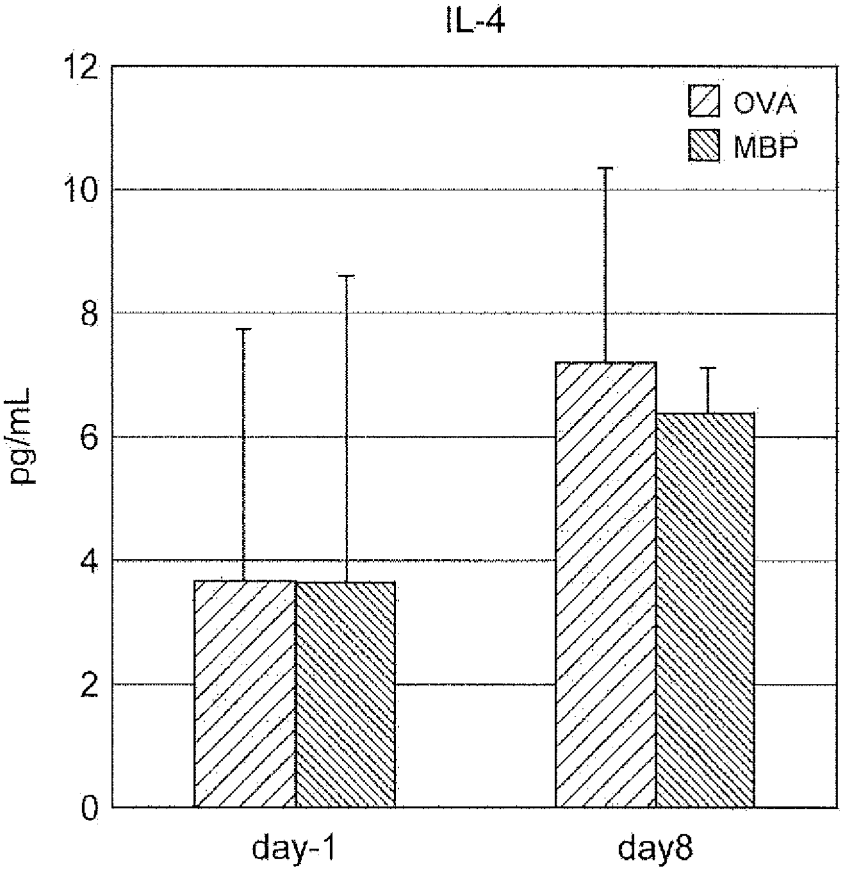
FIG. 7 is a diagram showing change in IL-4 expression level in a CD4-positive memory T-cell fraction ($CD3^+CD4^+CD45RA^-$) recovered by cell sorting from peripheral blood mononuclear cells prepared from MS patients orally given a single dose of compound 31 (0.3 mg administration), which is a synthetic glycolipid of the present invention. Also, day-1 represents one day before the administration of compound 31, and day8 represents 8 days after the administration of compound 31.
Figure 8:
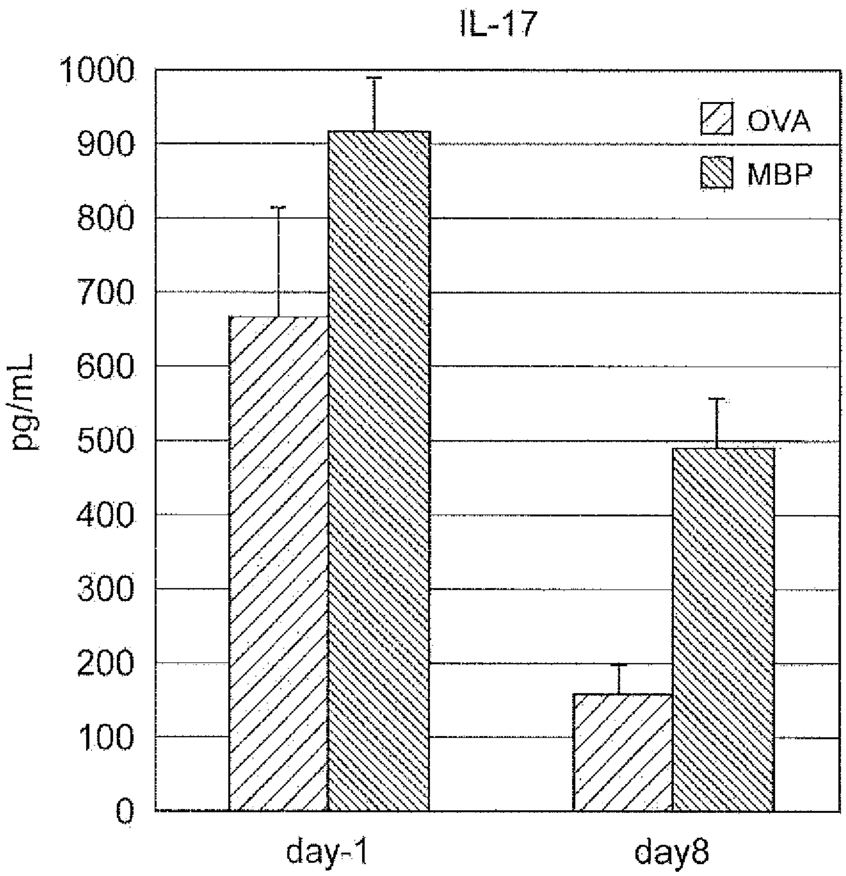
FIG. 8 is a diagram showing change in IL-17 expression level in a CD4-positive memory T-cell fraction ($CD3^+CD4^+CD45RA^-$) recovered by cell sorting from peripheral blood mononuclear cells prepared from MS patients orally given a single dose of compound 31 (0.3 mg administration), which is a synthetic glycolipid of the present invention. Also, day-1 represents one day before the administration of compound 31, and day8 represents 8 days after the administration of compound 31.
Figure 9:
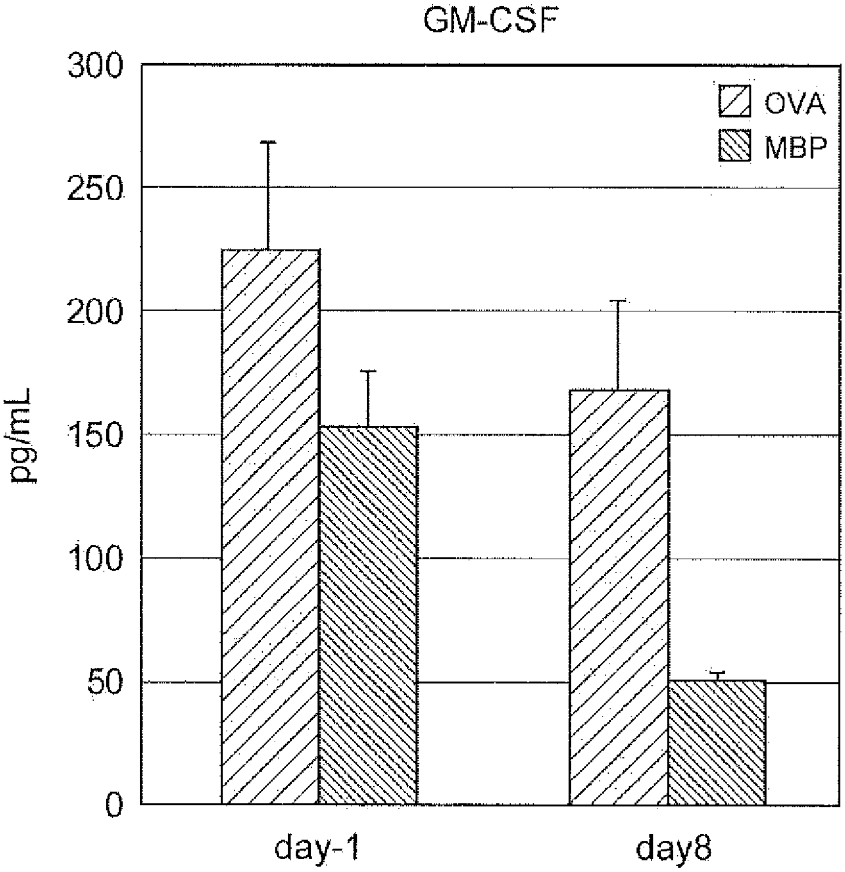
FIG. 9 is a diagram showing change in GM-CSF expression level in a CD4-positive memory T-cell fraction ($CD3^+CD4^+CD45RA^-$) recovered by cell sorting from peripheral blood mononuclear cells prepared from MS patients orally given a single dose of compound 31 (0.3 mg administration), which is a synthetic glycolipid of the present invention. Also, day-1 represents one day before the administration of compound 31, and day8 represents 8 days after the administration of compound 31.

The results about the abundance ratio of the GM-CSF-producing CD4-positive memory T-cells in PBMCs are shown in Table 3 and FIG. 5. In FIG. 5, the proportion of GM-CSF-producing CD4-positive memory T-cells decreased after the administration of compound 31 as compared with that before the administration of the compound 31 (day-1), indicating that the growth of CD4-positive memory T-cells was also suppressed or their ability to produce GM-CSF was also suppressed in MS patients by the administration of compound 31.

TABLE 3

| | Abundance ratio of mCD4T (%) |
|---|---|
| day −1 | 9.64 |
| day 1 | 6.035 |
| day 3 | 6.76 |
| day 7 | 14.325 |

Example 4: Activity Control of T-Cell in MS Patient

Objective

Activity-controlling effects on T-cells by the administration of the synthetic glycolipid of the present invention were verified in patients having multiple sclerosis (MS patients).

Method (1) Sorting and Staining

The collected PBMCs were stained with antibodies by the following method. First, 10 μL of a solution consisting of 20 μL of MACS buffer, 0.25 μL of APC-Cy7-anti-CD3 antibody (BioLegend, Inc.), 1 μL of PB-anti-CD4 antibody (BioLegend, Inc.), 1 μL of PerCP-Cy5.5-anti-CD45RA antibody (BioLegend, Inc.), and 1 μL of PC7-anti-CD56 antibody (Beckman Coulter, Inc.) was added to $6\times10^6$ cells of PBMCs, thoroughly mixed by vortexing, and then left on ice for 20 minutes. CD56 is a detection marker of cells having NK activity, and $CD3^-CD56^-$ cells indicate being antigen-presenting cells (APCs). 1 mL of MACS buffer was added, and after centrifugation at 1500 rpm for 5 minutes, a supernatant was removed by suction. The precipitate was resuspended in 500 μL of MACS buffer, then filtered, and subjected to flow cytometry analysis.

Cells contained in a cell zone exhibiting $CD3^+CD4^+CD45RA^-$ and cells contained in a $CD3^-CD56^-$ cell zone were respectively sorted and recovered. The cells of the cell zone exhibiting $CD3^+CD4^+CD45RA^-$ are a CD4-positive memory T-cell (rnCD4T) fraction. Likewise, the cells of the $CD3^-CD56^-$ cell zone is an antigen-presenting cell (APC) fraction.

(2) Cell Preparation mCD4T and APC obtained by the sorting were each suspended in a medium consisting of 500 mL of RPMI1640 (GIBCO/Thermo Fisher Scientific Inc.), 5 mL of glutamine (200 mM, Wako Pure Chemical Industries, Ltd.), 5 mL of Pen/strep (10,000 U/mL, GIBCO/Thermo Fisher Scientific Inc.), 0.5 mL of 2-mercaptoethanol (GIBCO/Thermo Fisher Scientific Inc.), and 50 mL of 10% (v/v) Cellect FETAL BOVINE SERUM (MP Biomedicals, LLC), and the number of cells was measured. Treatment by radiation (30 Gy) was performed as to APC.

(3) Culture

The cells prepared in the above (2) and each additive were added (each 50 μL/well) to a 96-well flat-bottom plate (BD Biosciences, product number: BD3072) so as to become ratios described in culture condition A or B shown in Table 4, and cultured at 37° C. for 6 hours in a 5% $CO_2$ incubator. In Table 4, OVA means ovalbumin, and MBP means myelin basic protein.

TABLE 4

| | Culture condition A | Culture condition B |
|---|---|---|
| mCD4T | $1 \times 10^4$ cells/well | $1 \times 10^4$ cells/well |
| APC | $1 \times 10^5$ cells/well | $1 \times 10^5$ cells/well |
| OVA | 10 μg/mL | — |
| MBP | — | 20 μg/mL |
| IL-2 | 20 U/mL | 20 U/mL |

(4) ELISA

After the culture, a culture supernatant was collected, and IFN-γ, IL-4, IL-17, and GM-CSF were measured by the ELISA method. The antibodies used in the ELISA method were an anti-IFN-γ antibody (BD Biosciences, product number: 555142, dilution ratio in use: 20-fold), an anti-IL-4 antibody (BD Biosciences, product number: 555194, dilution ratio in use: 4-fold), an anti-IL-17 antibody (R&D Systems, Inc., product number: DY317, dilution ratio in use: 4-fold), and an anti-GM-CSF antibody (BD Biosciences, product number: 555126, dilution ratio in use: 4-fold).

Results

The results are shown in Table 5 and FIGS. 6 to 9. FIGS. 6 to 9 are graphs showing the expression levels of various cytokines at the points in time of one day before the administration of compound 31 (day-1) and 192 hours after the administration (day8). As shown in FIGS. 6 to 9, the expression levels of IFN-γ, IL-4, IL-17, and GM-CSF were changed. Specifically, the expression levels of IFN-γ, IL-17, and GM-CSF decreased and the expression level of IL-4 increased by the administration of compound 31. Namely, it was revealed that Th1/Th2 balance was changed into a state in which Th2 was dominant. Also, because the difference was not observed between culture condition A (OVA stimulation) and culture condition B (MBP stimulation), it is considered that this change in the mode of cytokine expression is not specific for MBP and is change in the whole T-cells.

TABLE 5

| | | IFNγ | IL-4 | IL-17 | GM-CSF |
|---|---|---|---|---|---|
| day −1 | OVA | 23489.34 | 3.66 | 666.56 | 224.87 |
| | MBP | 28528.18 | 3.63 | 916.90 | 153.15 |
| day 8 | OVA | 5032.43 | 7.19 | 158.50 | 168.45 |
| | MBP | 7006.30 | 6.38 | 491.24 | 50.81 |

Example 5: Influence of Species Difference on Disposition of Compound

Objective

Time-dependent change in disposition when compound 31 was orally administered was compared among a mouse, a rat, a monkey, and humans.

Method

After a single dose of compound 31 labeled with $^{14}C$ was orally administered at a predetermined dose to each of a male mouse, a male rat, and a male cynomolgus monkey under fasting conditions, the concentration in blood was measured after a lapse of a given time, and parameters such as maximum plasma concentration $C_{max}$, time $T_{max}$ to reach the maximum plasma concentration, half-life $t_{1/2}$, area under curve $AUC_{0-\infty}$, mean retention time $MRT_{0-\infty}$, and bioavailability BA were calculated. The concentration in blood in humans (normal subjects) was measured and each of the parameters was calculated, in the similar manner as above except that $^{14}C$-unlabeled compound 31 was used.

Results

The results are shown in Tables 6 to 9. Table 6 shows time-dependent change in concentration in blood when a single dose was orally administered to the mouse (dose: 5 mg/kg), the rat (dose: 10 mg/kg), and the cynomolgus monkey (dose: 10 mg/kg). Table 7 shows the parameters calculated on the basis of the concentration in blood shown in Table 6. Table 8 shows time-dependent change in concentration in blood by oral administration to humans (dose: 0.3, 1, 3, 10, and 30 mg). Table 9 shows the parameters calculated on the basis of the concentration in blood shown in Table 8. In the tables, "N.D." means not detected.

TABLE 6

| | Dose | Time (h) | | | | | | | | | |
|---|---|---|---|---|---|---|---|---|---|---|---|
| | (mg/kg) | 4 | 8 | 12 | 24 | 48 | 72 | 96 | 120 | 144 | 168 |
| Mouse | 5 | 46.5 | 209 | 142 | 33 | 5.21 | 1.62 | — | — | — | N.D. |
| Rat | 10 | 31 | 128 | 101 | 47.1 | 18.5 | 10.2 | — | — | — | N.D. |

TABLE 6-continued

| | Dose | Time (h) | | | | | | | | | |
|---|---|---|---|---|---|---|---|---|---|---|---|
| | (mg/kg) | 4 | 8 | 12 | 24 | 48 | 72 | 96 | 120 | 144 | 168 |
| Cynomolgus monkey | 10 | 1.92 | 9.59 | 33.4 | 35.2 | 26.5 | 13 | 7.1 | 4.21 | 2.83 | 2.05 |

TABLE 7

| | Dose (mg/kg) | $C_{max}$ (ng/mL) | $T_{max}$ (h) | $t_{1/2}$ (h) | $AUC_{0-t}$ (ng · h/mL) | $AUC_{0-\infty}$ (ng · h/mL) | $MRT_{0-\infty}$ (h) | BA (%) | Rate of absorption (%) |
|---|---|---|---|---|---|---|---|---|---|
| Mouse | 5 | 209 | 8 | 11 | 2896 | 2922 | 15.4 | 1.01 | 1.36 |
| Rat | 10 | 128 | 8 | 26 | 3132 | 3330 | 32.4 | 0.51 | 0.96 |
| Cynomolgus monkey | 10 | 39.4 | 28 | 39.2 | 2260 | 2376 | 60.9 | 0.11 | 0.41 |

TABLE 8

| | Dose | Time (h) | | | | | | | | | |
|---|---|---|---|---|---|---|---|---|---|---|---|
| | (mg/body) | 6 | 13 | 21 | 24 | 30 | 36 | 48 | 72 | 96 | 144 |
| Human | 0.3 | 0.368 | 0.629 | 0.365 | 0.31 | 0.382 | N.D. | N.D. | N.D. | N.D | N.D. |
| | 1 | 0.368 | 1.39 | 1.04 | 0.98 | 0.961 | 1.01 | 0.719 | 0.484 | 0.224 | N.D. |
| | 3 | 0.337 | 1.13 | 1.33 | 1.33 | 1.7 | 1.99 | 1.37 | 0.838 | 0.549 | 0.266 |
| | 10 | 2.01 | 3.32 | 3.15 | 3.33 | 3.76 | 5.37 | 3.66 | 2.23 | 1.42 | 0.689 |
| | 30 | 2.82 | 6.65 | 6.98 | 7.47 | 8.08 | 9.46 | 6.58 | 4.65 | 3.05 | 1.82 |

TABLE 9

| | Dose (mg/body) | $C_{max}$ (ng/mL) | $T_{max}$ (h) | $t_{1/2}$ (h) | $AUC_{0-t}$ (ng · h/mL) | $AUC_{0-\infty}$ (ng · h/mL) |
|---|---|---|---|---|---|---|
| Human | 0.3 | 0.629 | 13 | 21.4 | 11.7 | 23.4 |
| | 1 | 1.49 | 20.7 | 44.3 | 63.4 | 87.1 |
| | 3 | 2.11 | 28.3 | 47.8 | 121 | 146 |
| | 10 | 6.01 | 26.3 | 45.3 | 324 | 381 |
| | 30 | 9.81 | 28.3 | 53.6 | 657 | 795 |

In this context, assuming the body weights of the humans were 60 kg, the doses were corrected to be the same, and the value of $AUC_{0-\infty}$ was compared between the mouse, the rat, and the cynomolgus monkey, and the humans. Results of calculating species difference (fold) according to an expression given below are shown in Table 10. As shown in Table 10, compound 31 exhibited a high concentration in blood at a very low dose in the humans as compared with the mouse, the rat, and the cynomolgus monkey. Specifically, $AUC_{0-\infty}$ for the humans was 2.72 to 8.94 times $AUC_{0-\infty}$ for the mouse, 4.77 to 15.7 times $AUC_{0-\infty}$ for the rat, and 6.69 to 22.0 times $AUC_{0-\infty}$ for the cynomolgus monkey.

$$\text{Species difference [fold]} = \frac{(\text{Human } AUC_{0-\infty})/(\text{Human dose [mg/body]/Body weight (60 [kg])}}{(\text{Mouse, rat, or cynomolgus monkey } AUC_{0-\infty})/(\text{Mouse, rat, or cynomologus monkey dose [mg/kg]}} \quad \text{[Expression 1]}$$

TABLE 10

| | | Mouse 5 mg/kg | Rat 10 mg/kg | Cynomolgus monkey 10 mg/kg |
|---|---|---|---|---|
| Human | 0.3 mg/body | 8.01 | 14.05 | 19.70 |
| | 1 mg/body | 8.94 | 15.69 | 21.99 |
| | 3 mg/body | 5.00 | 8.77 | 12.29 |
| | 10 mg/body | 3.91 | 6.86 | 9.62 |
| | 30 mg/body | 2.72 | 4.77 | 6.69 |

Example 6: Disposition of Compound in MS Patient

Objective

Time-dependent change in disposition when compound 31 was orally administered to MS patients was compared.

Method

In the similar manner as in Example 5, a single dose of compound 31 labeled with $^{14}C$ was orally administered to each of 2 MS patients (subjects) after obtainment of informed consent, and the concentration of the compound in blood was measured and each parameter was calculated by collecting blood after a lapse of a given time.

The results are shown in Table 11. In the table, "N.C." means not calculated. The disposition of compound 31 in the MS patients exhibited a low concentration in blood as compared with the disposition in normal persons. However, as with the data of Example 3, the pharmacological effects of compound 31 were also observed in Example 6.

TABLE 11

| | Dose (mg/body) | $C_{max}$ (ng/mL) | $T_{max}$ (h) | $t_{1/2}$ (h) | $AUC_{0-t}$ (ng · h/mL) | $AUC_{0-\infty}$ (ng · h/mL) |
|---|---|---|---|---|---|---|
| Human | 0.3 | 0.122 | 18 | N.C. | 1.41 | N.C. |

The invention claimed is:

1. A method for treating a disease caused by an increase in GM-CSF concentration in a human subject, comprising the step of orally administering an agent comprising the glycolipid compound represented by the formula (I) or a salt thereof in an amount selected from 0.01 mg to 1 mg per dosage as an active ingredient to a human subject in need thereof:

(I)

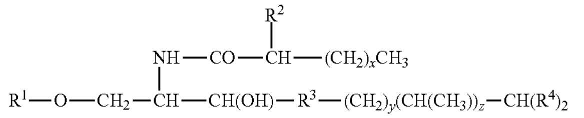

wherein $R^1$ represents an aldopyranose residue, $R^2$ represents a hydrogen atom or a hydroxy group, $R^3$ represents $—CH_2—$, $—CH(OH)—CH_2—$, or $—CH{=}CH—$, each $R^4$ independently represents a hydrogen atom or $CH_3$, x is an integer selected from 0 to 35, and y and z each represent an integer that satisfies y+z=0, 1, 2, or 3.

2. The method according to claim 1, wherein the glycolipid compound or salt thereof is administered in an amount selected from 0.05 mg to 1 mg per dosage to a human subject in need thereof.

3. The method according to claim 1, wherein $R^1$ is represented by the following formula (II):

(II)

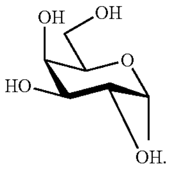

4. The method according to claim 1, wherein $R^3$ represents $—CH(OH)—CH_2—$.

5. The method according to claim 1, wherein $R^2$ and $R^4$ each represent a hydrogen atom, x is an integer selected from 11 to 23, and z is 0.

6. The method according to claim 1, wherein the disease caused by the increase in GM-CSF concentration is multiple sclerosis, chronic organ inflammation, or rheumatoid arthritis.

7. A method for treating a disease in which Th1/Th2 immune balance is directed toward Th1 in a human subject, the method comprising the step of orally administering an agent comprising the glycolipid compound represented by the formula (I) or a salt thereof in an amount selected from 0.01 mg to 1 mg per dosage as an active ingredient to a human subject in need thereof:

(II)

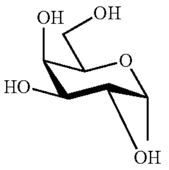

wherein $R^1$ represents an aldopyranose residue, $R^2$ represents a hydrogen atom or a hydroxy group, $R^3$ represents $—CH_2—$, $—CH(OH)—CH_2—$, or $—CH{=}CH—$, each $R^4$ independently represents a hydrogen atom or $CH_3$, x is an integer selected from 0 to 35, and y and z each represent an integer that satisfies y+z=0, 1, 2, or 3, and wherein the disease is selected from Crohn disease, vitiligo vulgaris, Behcet's disease, collagen disease, multiple sclerosis, rheumatoid arthritis, psoriasis, type I diabetes mellitus, uveitis, Sjogren's syndrome, autoimmune myocarditis, autoimmune liver disease, autoimmune gastritis, pemphigus, Guillain-Barre syndrome, chronic inflammatory demyelinating polyneuropathy, HTLV-1-related myelopathy, fulminant hepatitis, graft rejection, and infectious diseases caused by intracellular infectious pathogens.

* * * * *